US011898161B2

(12) United States Patent
Sasai et al.

(10) Patent No.: US 11,898,161 B2
(45) Date of Patent: *Feb. 13, 2024

(54) STEM CELL CULTURE MEDIUM AND METHOD

(71) Applicant: RIKEN, Wako (JP)

(72) Inventors: Yoshiki Sasai, Wako (JP); Kiichi Watanabe, Wako (JP)

(73) Assignee: RIKEN, Wako (JP)

( * ) Notice: Subject to any disclaimer, the term of this patent is extended or adjusted under 35 U.S.C. 154(b) by 291 days.

This patent is subject to a terminal disclaimer.

(21) Appl. No.: 16/852,361

(22) Filed: Apr. 17, 2020

(65) Prior Publication Data
US 2020/0239838 A1 Jul. 30, 2020

Related U.S. Application Data

(63) Continuation of application No. 15/250,848, filed on Aug. 29, 2016, now Pat. No. 10,626,366, which is a continuation of application No. 12/442,245, filed as application No. PCT/GB2007/003636 on Sep. 24, 2007, now abandoned.

(30) Foreign Application Priority Data

Sep. 22, 2006 (JP) ................................. 2006-257780
Apr. 27, 2007 (JP) ................................. 2007-118183
May 25, 2007 (GB) ....................................... 0710095

(51) Int. Cl.
C12N 5/00 (2006.01)
C12N 5/02 (2006.01)
C12N 5/0735 (2010.01)
C12N 5/073 (2010.01)
A01N 63/00 (2020.01)

(52) U.S. Cl.
CPC ......... C12N 5/0606 (2013.01); C12N 5/0603 (2013.01); C12N 2501/70 (2013.01); C12N 2501/999 (2013.01); C12N 2506/00 (2013.01)

(58) Field of Classification Search
CPC . C12N 5/0606; C12N 5/0603; C12N 2506/00
See application file for complete search history.

(56) References Cited

U.S. PATENT DOCUMENTS

| 7,109,032 B2 | 9/2006 | Cancedda et al. |
| 7,892,830 B2 | 2/2011 | Bergendahl et al. |
| 8,492,147 B2 | 7/2013 | Sasai et al. |
| 10,626,366 B2 * | 4/2020 | Sasai ............... C12N 5/0606 |
| 2008/0044901 A1 | 2/2008 | Sasai et al. |
| 2008/0113433 A1 | 5/2008 | Robins et al. |

FOREIGN PATENT DOCUMENTS

| EP | 2 066 786 A1 | 6/2009 |
| WO | WO 2003/046141 A2 | 6/2003 |
| WO | WO 2005/080394 A1 | 9/2005 |
| WO | WO 2005/123902 A1 | 12/2005 |
| WO | WO 2006/019366 A1 | 2/2006 |
| WO | WO 2006/053014 A2 | 5/2006 |
| WO | WO 2007/130664 A2 | 11/2007 |
| WO | WO 2008/035110 A1 | 3/2008 |

OTHER PUBLICATIONS

Amit et al., "Clonally Derived Human Embryonic Stem Cell Lines Maintain Pluripotency and Proliferative Potential for Prolonged Periods of Culture," *Developmental Biology*, 227: 271-278 (2000).
Chen et al., "Embryonic stem cells generated by nuclear transfer of human somatic nuclea into rabbit oocytes," *Cell Research*, 13(4): 251-263 (2003).
Eguchi et al., "Self-organizing cortex generated from human iPSCs with combination of FGF2 and ambient oxygen," *Biochem. Biophys. Res. Commun.*, 498(4): 729-735 (2018).
Eiraku et al., "Self-Organized Formation of Polarized Cortical Tissues from ESCs and Its Active Manipulation by Extrinsic Signals," *Cell Stem Cell*, 3(5): 519-532 (2008).
Fukushima et al., "Hydroxyfasudil, A Rho-Kinase (ROCK) Inhibitor, Suppresses Cell Growth and Collagen Production in Rat Hepatic Stellate Cells," *Hepatology*, 38: 562A, abstract 830 (2003).
Hertz et al., "Neuromethods: Series 1 : Neurochemistry—General Neurochemical Techniques," Humana Press (publisher), Boulton & Baker (editors), Chapter 4, Section 2.3.3, pp. 128-129 (1985).
Ishizaki et al., "Pharmacological Properties of Y-27632, a Specific Inhibitor of Rho-Associated Kinases," *Molecular Pharmacology*, 57(5): 976-983 (2000).
Koyanagi et al., "Inhibition of the Rho/ROCK Pathway Reduces Apoptosis During Transplantation of Embryonic Stem Cell-Derived Neural Precursors," *Journal of Neuroscience Research*, 86: 270-280 (2008).
Kurosawa, Hiroshi, "Application of Rho-associated protein kinase (ROCK) inhibitor to human pluripotent stem cells," *Journal of Bioscience and Bioengineering*, 114(6): 577-581 (2012).
Kuwahara et al., "Generation of a ciliary margin-like stem cell niche from self-organizing human retinal tissue," *Nat. Commun.*, 6: 6286 (2015).
Labosky et al., "Mouse embryonic germ (EG) cell lines: transmission through the germline and differences in the methylation imprint of insulin-like growth factor 2 receptor (Igf2r) gene compared with embryonic stem (ES) cell lines," *Development*, 120: 3197-3204 (1994).
Laplante et al., "RhoA/ROCK and Cdc42 Regulate Cell-Cell Contact and N-Cadherin Protein Level during Neurodetermination of P19 Embryonal Stems Cells," *Journal of Neurobiology*, 60: 289-307 (2004).

(Continued)

*Primary Examiner* — Quang Nguyen

(74) *Attorney, Agent, or Firm* — Leydig, Voit & Mayer, Ltd.

(57) ABSTRACT

The invention provides a method of differentiating human pluripotent stem cells to ectodermal cell by treating human pluripotent stem cells, which are dissociated single cells, and inducing differentiation to ectodermal cells under conditions where a ROCK(Rho-kinase) inhibitor is present in a culture medium in contact with the cells after dissociation of the human pluripotent stem cells.

16 Claims, 13 Drawing Sheets

(56) References Cited

OTHER PUBLICATIONS

Figure 1A:
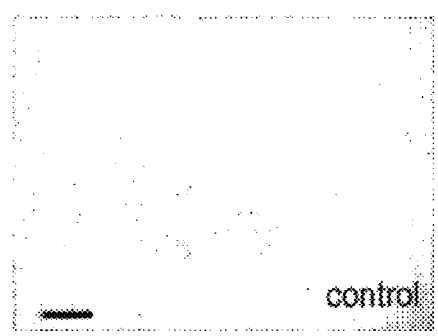
Figure 1B:
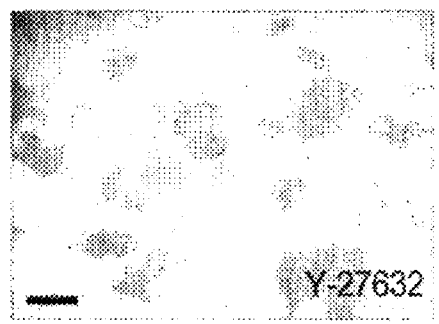
Figure 1C:
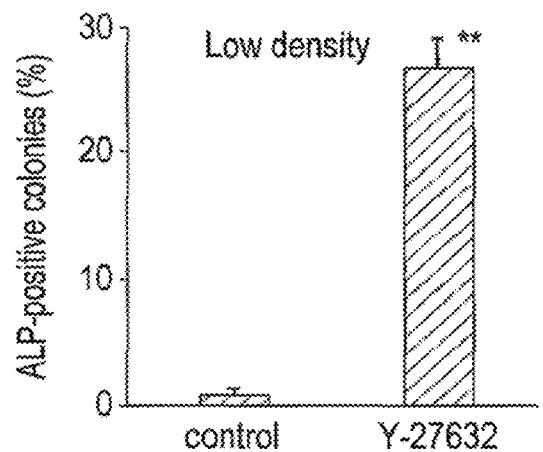
Figures 1D, 1E, 1F:
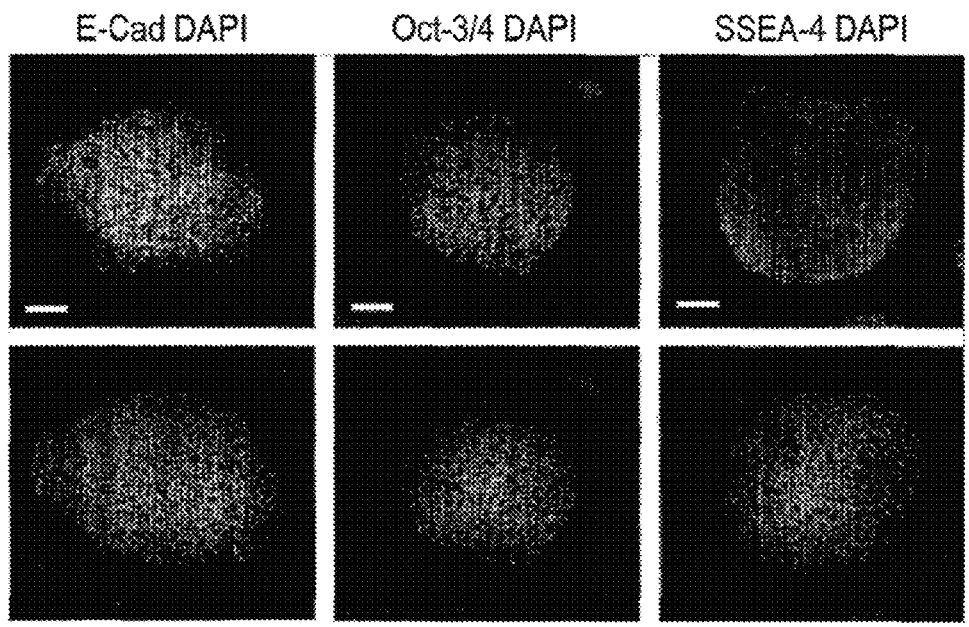
Figures 1G, 1H:
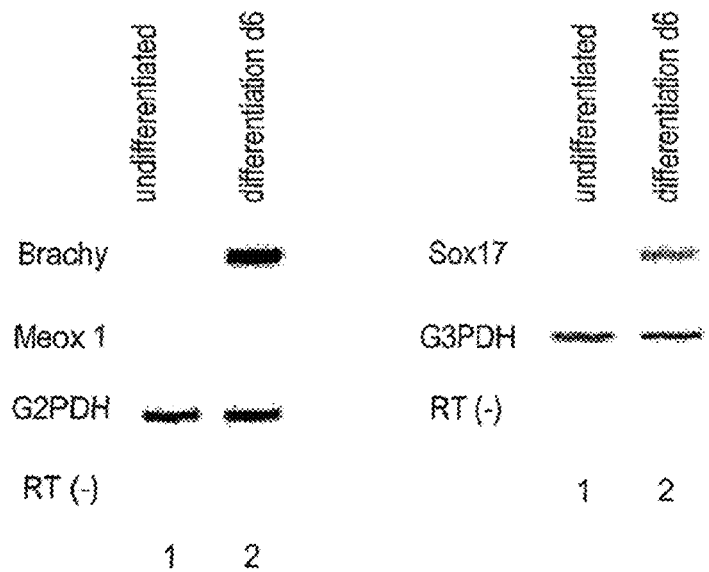
Figures 1I, 1J, 1K:
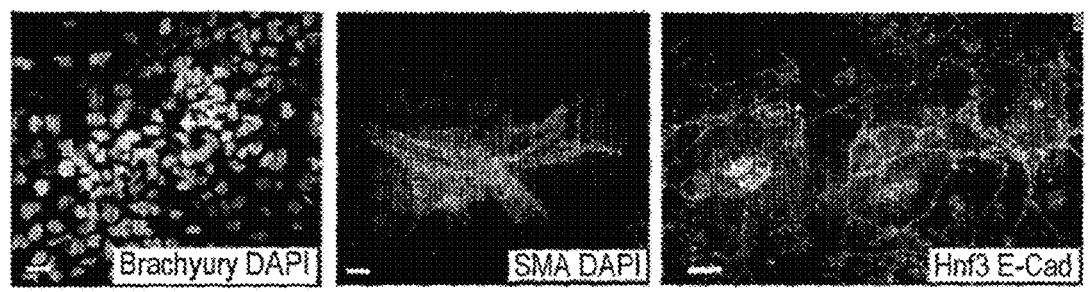

Liao et al., "Rho Kinase (ROCK) Inhibitors," *J. Cardiovasc. Pharmacol.*, 50(1): 17-24 (2007).
Mcbeath et al., "Cell Shape, Cytoskeletal Tension, and RhoA Regulate Stem Cell Lineage Commitment," *Dev. Cell*, 6(4): 483-495 (2004).
Miñambres et al., "The RhoA/ROCK-I/MLC pathway is involved in the ethanol-induced apoptosis by anoikis in astrocytes," *J. Cell Sci.*, 119(2): 271-282 (2005).
Muramatsu et al. (eds.), "Bunshi Saibou Seibutsu-gaku Jiten" (Molecular and Cellular Biology Dictionary), 2nd edition, Tokyo Kagaku Dojin (Oct. 10, 2008), p. 552, entry for "Pluripotent Stem Cell."
Nakano et al., "Self-Formation of Optic Cups and Storable Stratified Neural Retina from Human ESCs," *Cell Stem Cell*, 10(6): 771-785 (2012).
Niwa, Hitoshi, "Definitions of key words in stem cell biology," *Protein Nucleic Acid and Enzyme*, 51(11): 1610-1617 (2006).
Osakada et al., "In vitro differentiation of retinal cells from human pluripotent stem cells by small-molecule induction," *J. Cell Sci.*, 122: 3169-3179 (2009).
Ozone et al., "Functional anterior pituitary generated in self-organizing culture of human embryonic stem cells," *Nat. Commun.*, 7: 10351 (2016).
Pakzad et al., "Presence of a ROCK Inhibitor in Extracellular Matrix Supports More Undifferentiated Growth of Feeder-Free Human Embryonic and Induced Pluripotent Stem Cells upon Passaging," *Stem Cell Rev. and Rep*, 6: 96-107 (2010).
Pacary et al., "Synergistic effects ofCoCh and ROCK inhibition on mesenchymal stem cell differentiation into neuron-like cells," *Journal of Cell Science* 119: 2667-2678 (2006).
Park et al., "Reprogramming of human somatic cells to pluripotency with defined factors," *Nature*, doi:10.1038/nature06534 (Jun. 12, 2008).
Pouton et al., "Pharmaceutical applications of embryonic stem cells," *Adv. Drug Deliv. Rev.*, 57(13): 1918-1934 (2005).
Rattan et al., "Rho/ROCK pathway as a target of tumor therapy," *J. Neuro. Res.*, 83(2): 243-255 (2006).
Renau-Piqueras et al., "Effects of Prolonged Ethanol Exposure on the Glial Fibrillary Acidic Protein-containing Intermediate Filaments of Astrocytes in Primary Culture: A Quantitative Immunofluorescence and Immunogold Electron Microscopic Study," *J. Histochem. Cytochem.*, 37(2): 229-240 (1989).
Svoboda et al., "Rock inhibitor (Y27632) increases apoptosis and disrupts the actin cortical mat in embryonic avian corneal epithelium," *Developmental Dynamics*, 229(3): 579-590 (2004).
Takahashi et al., "Induction of Pluripotent Stem Cells from Mouse Embryonic and Adult Fibroblast Cultures by Defined Factors," *Cell*, 126: 663-676 (Aug. 25, 2006).
Takehara et al., "Rho-associated kinase inhibitor Y-27632 promotes survival of cynomolgus monkey embryonic stem cells," *Molecular Human Reproduction*, 14(11): 627-634 (2008).
Watanabe et al., "Directed differentiation of telencephalic precursors from embryonic stem cells," *Nature Neuroscience*, 8(3): 288-296 with supplementary figures 1-8 and descriptions therefor (Mar. 2005).
Watanabe et al., "A Rock inhibitor permits survival of dissociated human embryonic stem cells," *Nature Biotechnology*, 25: 681-686 (2007).
Vichalkovski et al., "Two different pathways link G-protein-coupled receptors with tyrosine kinases for the modulation of growth and survival in human hematopoietic progenitor cells," *Cell Signal*, 17: 447-459 (2005).
European Patent Office, International Search Report for International Patent Application No. PCT/GB2007/003636 (dated Dec. 10, 2007).
U.S. Appl. No. 15/250,848, filed Aug. 29, 2016.
U.S. Appl. No. 12/442,245, filed Jul. 13, 2009.
Doi et al., "Isolation of Human Induced Pluripotent Stem Cell-Derived Dopaminergic Progenitors by Cell Sorting for Successful Transplantation," *Stem Cell Reports*, 2(3): 337-350 (2014).
Hackland et al., "Top-Down Inhibition of BMP Signaling Enables Robust Induction of hPSCs Into Neural Crest in Fully Defined, Xeno-free Conditions," *Stem Cell Reports*, 9(4): 1043-1052 (2017).
Kuwahara et al., "Generation fo a Ciliary Margin-like Stem Cell Niche from Self-organizing Human retinal Tissue," *Nature Communications*, 6: 6286 (2015).
Saito-Diaz et al., "Derivation of Peripheral Nociceptive, Mechanoreceptive, and Proprioceptive Sensory Neurons from the same Culture of Human Pluripotent Stem Cells," *Stemm Cell Reports*, 16(3): 446-457 (2021).
Watanabe et al., "A ROCK Inhibitor Permits Survival of Dissociated Human Embryonic Stem Cells," *Nature Biotechnology*, 25(6): 681-686 (2007).

* cited by examiner

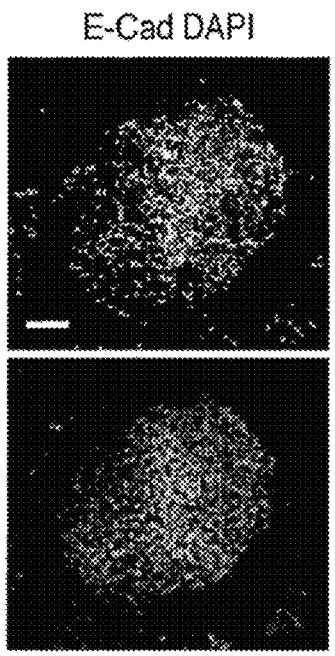
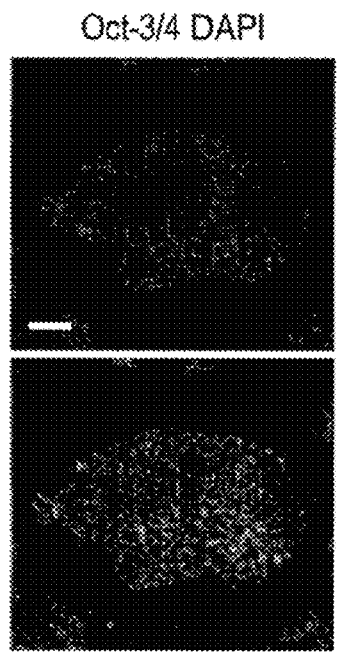
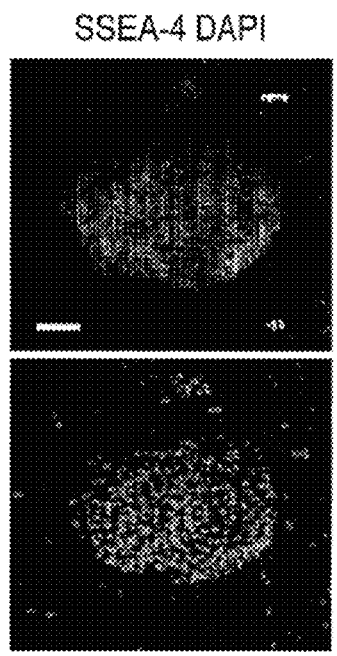
Fig. 4A  Fig. 4B  Fig. 4C
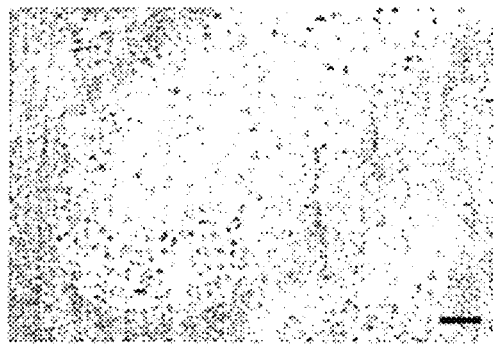
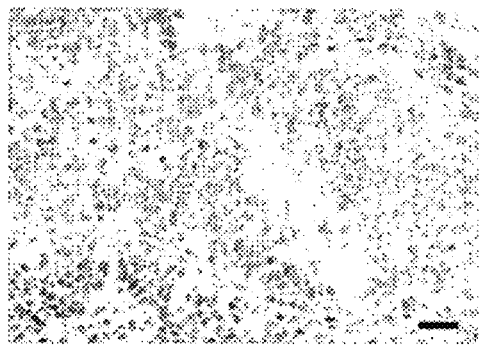
Fig. 4D  Fig. 4E
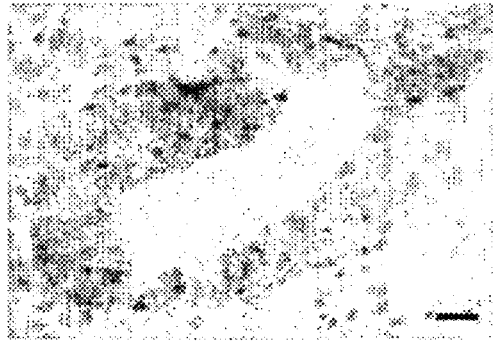
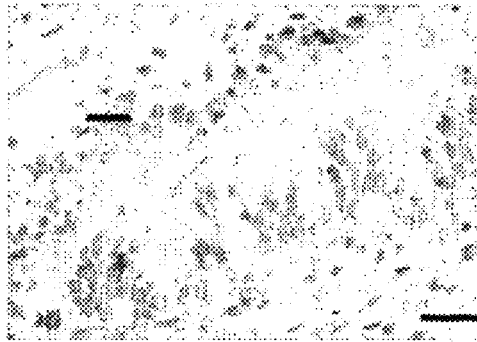
Fig. 4F  Fig. 4G

STEM CELL CULTURE MEDIUM AND METHOD

CROSS-REFERENCE TO RELATED APPLICATIONS

This patent application is a continuation of copending U.S. patent application Ser. No. 15/520,848, filed on Aug. 29, 2016, which is a continuation of U.S. patent application Ser. No. 12/442,245, filed on Jul. 13, 2009, which is the U.S. national phase of International Patent Application No. PCT/GB07/03636, filed Sep. 24, 2007, which claims the benefit of Japanese Patent Application No. 2006-257780, filed on Sep. 22, 2006, Japanese Patent Application No. 2007-118183, filed on Apr. 27, 2007, and United Kingdom Patent Application No. 0710095.1, filed on May 25, 2007, which are incorporated by reference in their entireties herein.

The present invention provides a method of culturing stem cells such as embryonic stem cells (ES cells), a medium for culture of such stem cells and uses thereof.

ES cells provide a strong candidate as a cell source in cell transplants for central nervous disease such as Parkinson's disease and diabetes. In study of ES cells, mouse ES cell are commonly used at present, but in view of clinical applications, it is necessary to carry out research and development not using human ES cells. However, human ES cells more easily undergo cell death than mouse ES cells in cell culture.

For example, in subculture of human ES cells in maintenance culture, cell aggregates are suspended once they have been detached from feeder cells or substrates by enzyme treatment or mechanical detachment, separated by pipetting to small cell aggregates, and then seeded to a new culture plate. However, human ES cells undergo detachment and dissociation poorly in comparison with common cell strains and mouse ES cells, and many of the cells do not survive. Since human ES cells divide very slowly and differentiate easily, a lot of time and manpower is required for culturing human ES cells while keeping their undifferentiated properties and technical training is required to obtain reproducible results. Furthermore, an impediment to research and development using human ES cells is that the collection rate is lowered because of cell death in subculture. Further, whilst it is desired to clone human ES cells in genetic engineering processes, when human ES cells are homogeneously dissociated into single cells cell death and cessation of growth occurs very easily and cloning efficiency in human ES cells is consequently believed to be 1% or less.

Further, to differentiate human ES cells they are detached from feeder cells, dissociated as small cell aggregates or single cells then plated on a substrate or specific feeder cells and cultured in differentiation inducing medium. This process has a very low efficiency. Further, in an embryoid culture method, a SFEB (Serum-free Floating culture of Embryoid Bodies-like aggregates) method developed by the present inventor (WO 2005/123902 and Watanabe et al., Nature Neuroscience 8, 288-296 (2005)), it is required that cells are dissociated into single cells once and cell aggregates are formed, but when such a methodology is applied to human ES cells a lot of cells die. Further, there is a problem in case of human ES cells that even if they are not completely singly-dissociated (in case of culturing from small cell aggregates), the cells die at high frequency—Frisch et al., Curr. Opin. Cell Biol. 13, 555-562 (2001)). Accordingly, the development of improved methodology for culture of human ES cells is desired.

Rho-associated coiled-coil kinase (ROCK:GenBank accession NO:NM_005406) is one of the main effector molecules of Rho GTPase and it is known that it controls physiological phenomena such as vascular constriction and nerve axon extension (Riento et al., Nat. Rev. Mol. Cell. Biol. 4, 446-456 (2003)). Several compounds are known as the ROCK inhibitors (for example, Ishizaki et al., Mol. Pharmacol. 57, 976-983 (2000) and Narumiya et al., Methods Enzymol. 325, 273-284 (2000)). Although there are several reports that the cellular death is controlled by ROCK inhibition (Minambres et al., J. Cell Sci. 119, 271-282 (2006) and Kobayashi et al., J. Neurosci. 24, 3480-3488 (2004)), there are also reports that ROCK inhibition accelerates apoptosis (Rattan et al., J. Neurosci Res. 83, 243-255 (2006) and Svoboda et al., Dev Dyn. 229, 579-590 (2004)) and the role of Rho/ROCK in apoptosis control is not established yet (Riento et al., Nat. Rev. Mol. Cell. Biol. 4, 446-456 (2003)).

It is known from Pacary E. et al, J. Cell Science 119 (13) pp 2667-2678 that $CoCl_2$ induces differentiation of mesenchymal stem cells into neurons and that ROCK inhibition potentiates this effect. There is no report, however, with respect to the culture of stem cells such as ES cells in a medium containing a ROCK inhibitor.

An object of the present invention is to provide a novel methodology and novel medium effective for culturing stem cells such as ES cells.

The present inventors have extensively studied and as a result have found that the survival rate, proliferation potency and/or differentiation efficiency of a stem cell such as a pluripotent stem cell, especially an ES, cell can be improved by culturing the stem cell in a culture medium containing a ROCK inhibitor.

The present invention hence provides:—

[1] A method of culturing stem cells, which comprises a step of treating the stem cell with a ROCK inhibitor in a culture medium;

[2] The method of the above-mentioned [1], wherein the stem cells are embryonic stem cells;

[3] The method of the above-mentioned [1] or [2], wherein the stem cells are primate stem cells;

[4] The method of the above-mentioned [3], wherein the stem cells are human stem cells;

[5] The method of any of the above-mentioned [1]-[4], wherein the stem cells are dissociated;

[6] The method of the above-mentioned [5], wherein the dissociated stem cells are single cells or aggregated stem cells (i.e. cells having formed a cell clump);

[7] The method of any of the above-mentioned [1]-[6], which comprises a step of dissociating the stem cells, and a step of treating the stem cells with a ROCK inhibitor;

[8] The method of the above-mentioned [7], wherein the stem cells are treated with a ROCK inhibitor before the dissociation of the stem cells;

[9] The method of the above-mentioned [7] or [8], wherein the stem cells are treated with a ROCK inhibitor after the dissociation of the stem cells;

[10] The method of any of the above-mentioned [1]-[9], wherein the ROCK inhibitor is Y-27632, Fasudil, or H-1152;

[11] The method of any of the above-mentioned [1]-[10], wherein the cells are cultured in adherent culture or suspension culture;

[12] The method of any of the above-mentioned [1]-[11], wherein the culturing is passage culture or differentiation inducing culture;

[13] The method of any of the above-mentioned [1]-[12], used for (a) purification or cloning of the stem cell, (b) production of a genetically modified strain of the stem cell or (c) production of neural cells by suspension culture;

[14] The method of the above-mentioned [13], wherein the neural cells are forebrain neural cells;

[15] A method for producing a differentiated cell from a stem cell which has an improved survival rate and/or proliferation potency or a stem cell which has improved differentiation efficiency, said method comprising culturing a stem cell in the presence of a ROCK inhibitor;

[16] A method of treating a stem cell with a ROCK inhibitor;

[17] A cell preparation comprising a stem cell and a ROCK inhibitor;

[18] The cell preparation of the above-mentioned [17], wherein the stem cell is dissociated;

[19] A stem cell culture medium, comprising a ROCK inhibitor;

[20] A serum-free medium comprising a ROCK inhibitor; and

[21] A culture system containing a stem cell and a ROCK inhibitor in a medium.

Embodiments of the above thus include a method of culture of a stem cell comprising maintaining the stem cell in a culture medium comprising a ROCK inhibitor, and a stem cell culture medium comprising a ROCK inhibitor.

In further aspects, the invention provides: a method of culturing stem cells so as to promote cloning efficiency or passaging efficiency, comprising culturing the stem cells in a culture medium comprising a ROCK inhibitor; a method of promoting colony formation in a stem cell culture, comprising culturing stem cells in the presence of a ROCK inhibitor; and a method of improving cloning efficiency or passaging efficiency in a stem cell culture, comprising culturing stem cells in the presence of a ROCK inhibitor.

In preferred embodiments of the invention, the stem cells are cultured in the absence of feeder cells, feeder cell extracts and/or serum. The stem cells can be cultured in the presence of a ROCK inhibitor prior to subcloning or passaging, e.g. for at least one hour before subcloning or passaging. Alternatively or additionally, the stem cells are maintained in the presence of a ROCK inhibitor after subcloning or passaging. In preferred embodiments, the stem cells are maintained in the presence of a ROCK inhibitor for at least about 12 hours, more preferably at least about 2, about 4, or about 6 days. In other embodiments, the stem cells are maintained in the presence of a ROCK inhibitor for at least one to five passages.

In some embodiments of the invention, the ROCK inhibitor is subsequently withdrawn from the culture medium, for example after about 12 hours or after about 2, about 4, or about 6 days. In other embodiments, the ROCK inhibitor is withdrawn after at least one to five passages.

Another aspect of the invention provides a method of improving the survival of stem cells in a culture, comprising contacting the stem cells with or otherwise exposing the stem cells to a ROCK inhibitor. The methods of this aspect of the invention are particularly suitable for improving cell survival when the culture comprises dissociated stem cells or aggregates of stem cells in suspension. Such methods are especially useful when the culture comprises cells at low density, including the exemplary cell densities described herein, or when the culture comprises stem cells at clonal density. Preferably, the stem cells are maintained in the presence of a ROCK inhibitor for at least about 12 hours, more preferably for at least about 2, about 4, or about 6 days, or for at least one to five passages. Optionally, the ROCK inhibitor is subsequently withdrawn from the culture medium, e.g. after about 12 hours, after about 2, about 4, or about 6 days, or after at least one to five passages. An additional method of the invention is a method of transporting stem cells comprising transporting the stem cells in a medium comprising a ROCK inhibitor.

According to the present invention, it is preferred that the stem cells are pluripotent stem cells, e.g. embryonic stem cells, including any type of stem cell described herein. The stem cells can be adult multipotent stem cells. The stem cells can be murine stem cells, rodent stem cells or primate stem cells, including human stem cells.

It will be appreciated that the methods of the invention can be carried out using any suitable ROCK inhibitor as described herein. Preferred ROCK inhibitors are Y-27632, Fasudil and H-1152.

In another aspect, the invention provides a method of culture of ES cells, comprising the steps of:— maintaining the ES cells in a pluripotent state in culture, optionally on feeders;

passaging the ES cells at least once;

withdrawing serum or serum extract (if present) from the medium and withdrawing the feeders (if present) so that the medium is free of feeders, serum and serum extract; and subsequently maintaining the ES cells in a pluripotent state in the presence of a ROCK inhibitor.

Preferably, the ES cells are cultured in the presence of a ROCK inhibitor prior to withdrawal of the serum, serum extract and/or feeders;

The methods of the invention can advantageously be used in any situation in which stem cells are isolated or cultured at low densities. In use of the invention, the stem cells are maintained in an undifferentiated state with reduced cell death. Thus, the methods can be used to improve the derivation of stem cells from tissues. The methods of the invention can also be used for deriving pluripotent cells (e.g. ES cells including mouse and human ES cells) from a blastocyst using any appropriate methodology. For example, a blastocyst can be obtained and optionally be cultured in the presence of a ROCK inhibitor, after which the inner cell mass can be dissociated, a cell or cells from the inner cell mass isolated and cultured in the presence of a ROCK inhibitor.

The methods of the invention are also useful in the context of genetic modification of stem cells, particularly in isolating clonal populations of genetically modified stem cells. Accordingly, the invention provides a method of obtaining a transfected population of ES cells, comprising:— transfecting ES cells with a construct encoding a selectable marker;

plating the ES cells;

culturing the ES cells in the presence of a ROCK inhibitor; and selecting for cells that express the selectable marker.

The ROCK inhibitor can be present in the culture medium before and/or after the application of selection for cells that express the selectable marker. It is preferred that the ROCK inhibitor is present during selection, particularly if the selectable marker confers resistance to particular selection agents present in the medium (e.g. antibiotic resistance) to counteract the effects of low stem cell densities. Optionally the method further includes the step of subcloning the ES cells that express the selectable marker in the presence of a ROCK inhibitor, thereby promoting stem cell growth and/or colony formation and/or improving the survival of the stem cells.

The invention also provides use of a ROCK inhibitor in the manufacture of a culture medium for stem cells. For example, the culture medium can be any medium described herein, or can comprise a combination or one or more medium components described herein. The medium can be formulated so as to be suitable for the culture of any stem cell type described herein, including human and mouse stem cells, e.g. ES cells.

In a related aspect, the invention provides cell culture medium that is free of serum and serum extract and comprises: basal medium; a ROCK inhibitor; and optionally one or more of insulin, insulin growth factor and an iron transporter. Suitable basal media and iron transporters (e.g. transferrin) are readily available to the skilled person, including the exemplary media and iron transporters described herein.

Addition aspects of the present invention relate to the use of a ROCK inhibitor to achieve the effects on stem cells described herein. In particular, aspects of the invention provide use of a ROCK inhibitor to promote and/or improve cloning efficiency or passaging efficiency in a stem cell culture; use of a ROCK inhibitor to promote and/or improve colony formation in a stem cell culture; and use of a ROCK inhibitor to promote and/or improve the survival of stem cells in a culture It will be appreciated that discussion of the advantages of the methods of the invention provided herein applies equally to the use of ROCK inhibitors according to the invention and to media and other compositions according to the invention.

The culture methods of the present invention can improve the survival rate, proliferation potency or differentiation efficiency of stem cells, in particular, ES cells such as human ES cells. In particular, the culture method of the present invention can exhibit its advantages, for example, in any culture methods including dissociation of stem cells, adherent or suspension cultures of the dissociated stem cells or the like. The culture method of the present invention has such advantages, so that it can be preferably used for passage culture of the stem cell, differentiation inducing of the stem cell (for example, to neural or nerve cells), purification or cloning of the stem cell, genetic modification of the stem cell, and so on.

The cell preparation, culturing agent, combination (for example, composition and kit), serum-free medium, culture system and the like of the present invention can be preferably used, for example, for the culture method of the present invention.

The present invention provides a method of culturing a stem cell including treating the stem cell with a ROCK inhibitor, and a stem cell obtained by the culture method and differentiated cell therefrom. Further, the present invention provides a method of treating a stem cell with a ROCK inhibitor.

The term stem cell includes pluripotent, undifferentiated cells and includes embryonic stem cells (ES cells) and adult stem cells. Reference to ES cells includes ES cells established by culturing an early embryo before implantation, ES stem cells established by culturing an early embryo prepared by nuclear-transfer using a nucleus of a somatic cell, and ES cells having genes modified by genetic engineering. Such stem cells can be prepared by any of known methods (see, for example, Wilmut et. al., Nature, 385, 810 (1997); Cibelli et. al., Science, 280, 1256 (1998); Baguisi et. al., Nature Biotechnology, 17, 456 (1999); Wakayama et. al., Nature, 394, 369 (1998); Wakayama et. al., Nature Genetics, 22, 127 (1999); Wakayama et. al., Proc. Natl. Acad. Sci. USA, 96, 14984 (1999); Rideout et. al., Nature Genetics, 24, 109 (2000); Manipulating the Mouse Embryo A Laboratory Manual, Second Edition, Cold Spring Harbor Laboratory Press (1994); Gene Targeting, A Practical Approach, IRL Press at Oxford University Press (1993); and International Publication No. 01/088100). Further, embryonic stem cells are available from specified organizations or commercially available. For example, human ES cell such as KhES-1, KhES-2 and KhES-3 are available from Institute for Frontier Medical Sciences, Kyoto University. The term adult stem cell includes any stem cells capable of differentiating to differentiated cells described later. Neural stem cells, haematopoietic stem cells and mesenchymal stem cells are preferred examples of adult stem cells.

The stem cell can be derived from warm-blooded animals such as mammals (for example, primates, Rodentia). In more detail, mammals includes humans, monkeys, mice, rats, guinea pigs, hamsters, rabbits, cats, dogs, sheep, pigs, cattle, horses and goats. The stem cells are preferably derived from primates such as human.

The stem cells to be treated with a ROCK inhibitor according to the present invention can be dissociated cells or non-dissociated cells. The dissociated cells refer to cells treated to promote cell dissociation (for example, the dissociation described later). Dissociated cells include a single cell and cells having formed a small cell clump (aggregate) of several (typically about 2 to 50, 2 to 20, or 2 to 10) cells. The dissociated cells can be suspended (floating) cells or adhered cells. For example, it has been known that ES cells such as human ES cells are susceptible to specific conditions such as dissociation (and/or suspension culture after dissociation). The methods of the present invention have particular use when the stem cell is subject to conditions at which hitherto cell death would have occurred.

To practice the present invention ROCK inhibitors generally are suitable without limitation so long as an inhibitor can inhibit the function of Rho-kinase (ROCK), and suitable inhibitors include Y-27632 (for example, refer to Ishizaki et. al., Mol. Pharmacol. 57, 976-983 (2000); Narumiya et. al., Methods Enzymol. 325,273-284 (2000)), Fasudil (also referred to as HA1077) (for example, refer to Uenata et. al., Nature 389: 990-994 (1997)), H-1152 (for example, refer to Sasaki et. al., Pharmacol. Ther. 93: 225-232 (2002)), Wf-536 (for example, refer to Nakajima et. al., Cancer Chemother Pharmacol. 52(4): 319-324 (2003)), Y-30141 (described in U.S. Pat. No. 5,478,838) and derivatives thereof, and antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can be also used in the present invention (for example, refer to United State Patent Application Nos. 20050209261, 20050192304, 20040014755, 20040002508, 20040002507, 20030125344 and 20030087919, and International Patent Publication Nos. 2003/062227, 2003/059913, 2003/062225, 2002/076976 and 2004/039796). In the present invention, a combination of one or two or more of the ROCK inhibitors can also be used.

According to the present invention, the stem cell can be treated with the ROCK inhibitor in a medium. Thereby, the medium used in the methods of the present invention may already contain the ROCK inhibitor or alternatively, the methods of the present invention may involve a step of adding the ROCK inhibitor to the medium. The concentration of the ROCK inhibitor in the medium is particularly not limited as far as it can achieve the desired effects such as the improved survival rate of stem cells. For example, when Y-27632 is used as the ROCK inhibitor, it can be used at the concentration of preferably about 0.01 to about 1000 μM, more preferably about 0.1 to about 100 μM, further more preferably about 1.0 to about 30 µM, and most preferably about 2.0 to 20 µM. When Fasudil/HA1077 is used as the ROCK inhibitor, it can be used at about twofold the aforementioned Y-27632 concentration. When H-1152 is used as the ROCK inhibitor, it can be used at about $\frac{1}{50}^{th}$ of the aforementioned Y-27632 concentration.

The time for treating with the ROCK inhibitor is particularly not limited as long as it is a time duration for which the desired effects such as the improved survival rate of stem cells can be achieved. For example, when the stem cell is a human embryonic stem cell, the time for treating is preferably about 30 minutes to several hours (e.g., about one hour) before dissociation. After dissociation, the human embryonic stem cell can be treated with the ROCK inhibitor for, for example, about 12 hours or more to achieve the desired effects.

The density of the stem cell(s) to be treated with the ROCK inhibitor is particularly not limited as far as it is a density at which the desired effects such as the improved survival rate of stem cells can be achieved. It is preferably about $1.0 \times 10^1$ to $1.0 \times 10^7$ cells/ml, more preferably about $1.0 \times 10^2$ to $1.0 \times 10^7$ cells/ml, further more preferably about $1.0 \times 10^3$ to $1.0 \times 10^7$ cells/ml, and most preferably about $3.0 \times 10^4$ to $1.0 \times 10^6$ cells/ml.

The methods of the present invention can further involve a step of dissociating stem cells. Stem cell dissociation can be performed using any known procedures. These procedures include treatments with a chelating agent (such as EDTA), an enzyme (such as trypsin, collagenase), or the like, and operations such as mechanical dissociation (such as pipetting). The stem cell(s) can be treated with the ROCK inhibitor before and/or after dissociation. For example, the stem cell(s) can be treated only after dissociation. The treatment of the stem cell(s) with the ROCK inhibitor can be as described above.

The culturing conditions according to the present invention will be appropriately defined depending on the medium and stem cells used. The present invention also provides a medium to be used in the methods of the present invention.

The medium according to the present invention can be prepared using a medium to be used for culturing animal cells as its basal medium. As the basal medium, any of BME, BGJb, CMRL 1066, Glasgow MEM, Improved MEM Zinc Option, IMDM, Medium 199, Eagle MEM, aMEM, DMEM, Ham, RPMI 1640, and Fischer's media, as well as any combinations thereof can be used, but the medium is not particularly limited thereto as far as it can be used for culturing animal cells.

The medium according to the present invention can be a serum-containing or serum-free medium. The serum-free medium refers to media with no unprocessed or unpurified serum and accordingly, can include media with purified blood-derived components or animal tissue-derived components (such as growth factors). From the aspect of preventing contamination with heterogeneous animal-derived components, serum can be derived from the same animal as that of the stem cell(s).

The medium according to the present invention may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'thiolglycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium of the present invention can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and preferably about 0.1 to 0.5 mM, but the concentration is particularly not limited thereto as long as it is appropriate for culturing the stem cell(s).

A culture vessel used for culturing the stem cell(s) can include, but is particularly not limited to: flask, flask for tissue culture, dish, petri dish, dish for tissue culture, multi dish, micro plate, micro-well plate, multi plate, multi-well plate, micro slide, chamber slide, schale, tube, tray, culture bag, and roller bottle, as long as it is capable of culturing the stem cells therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, laminin, and fibronectin and mixtures thereof for example Matrigel, and lysed cell membrane preparations (Klimanskaya I et al 2005. Lancet 365: p 1636-1641).

Other culturing conditions can be appropriately defined. For example, the culturing temperature can be about 30 to 40° C. and preferably about 37° C. but particularly not limited to them. The $CO_2$ concentration can be about 1 to 10% and preferably about 2 to 5%. The oxygen tension can be 1-10%.

The methods of the present invention can be used for adhesion culture of stem cells, for example. In this case, the cells can be cultured in the presence of feeder cells. In the case where the feeder cells are used in the methods of the present invention, stromal cells such as foetal fibroblasts can be used as feeder cells (for example, refer to; Manipulating the Mouse Embryo A Laboratory Manual, Second Edition, Cold Spring Harbor Laboratory Press (1994); Gene Targeting, A Practical Approach, IRL Press at Oxford University Press (1993); Martin, Proc. Natl. Acad. Sci. USA, 78, 7634 (1981); Evans et. Al., Nature, 292, 154 (1981); Jainchill et al., J. Viral., 4, 549 (1969); Nakano et al., Science, 272, 722 (1996); Kodama et al., J. Cell. Physiol., 112, 89 (1982); and International Publication Nos. 01/088100 and 2005/080554).

The methods of the present invention can be also used for a suspension culture of stem cells, including suspension culture on carriers (Fernandes A M et al J Biotechnology 2007) or gel/biopolymer encapsulation (United States Patent 20070116680). The term suspension culture of the stem cells means that the stem cells are cultured under non-adherent condition with respect to the culture vessel or feeder cells (if used) in a medium. The suspension culture of stem cells includes a dissociation culture of stem cells and an aggregate suspension culture of stem cells. The term dissociation culture of stem cells means that suspended stem cells is cultured, and the dissociation culture of stem cells include those of single stem cell or those of small cell aggregates composed of a plurality of stem cells (for example, about 2 to, 20 cells). When the aforementioned dissociation culture is continued, the cultured, dissociated cells form a larger aggregate of stem cells, and thereafter an aggregate suspension culture can be performed. The aggregate suspension culture includes an embryoid culture method (see Keller et al., Curr. Opin. Cell Biol. 7, 862-869 (1995)), and a SFEB method (Watanabe et al., Nature Neuroscience 8, 288-296 (2005); International Publication No. 2005/123902). The methods of the present invention can significantly improve the survival rate and/or differentiation efficiency of stem cells in a suspension culture.

The methods of the present invention can be used as stem cell subculture methods. Therefore, the methods of the present invention can involve a step of collecting/plating stem cells. According to the methods of the present invention, a higher survival rate and improved proliferation potency can be achieved. For example, conventionally, the survival rate of the dissociated human ES cells was very low and could not be grown sufficiently. According to the methods of the present invention, the higher survival rate of the human ES cells and improved proliferation potency can be achieved. Accordingly, the methods of the present invention not only facilitate the culture of a large amount of human ES cells, which has been difficult, but also allow single cells (or a small aggregation of cells) to be dissociated from each other in culture efficiently; furthermore, the methods of the invention can promote the efficiency of drug discovery and safety tests (for example, high throughput screening) using stem cells. In addition, the methods of the present invention provide for easy screening/subcloning of genetically-modified stem cells (knocked-in and/or homologously-recombined cells) and safer and more homogeneous screening of a stem cell line for medical applications. The methods of the present invention also have advantages in that they result in the stem cells retaining undifferentiated properties of stem cells without impairing their differentiation potency.

The methods of the present invention can be used whilst inducing stem cell differentiation. Therefore, the methods of the present invention can involve a step of inducing stem cell differentiation. Any known method can be employed for inducing stem cell differentiation. Examples of the cells to be produced through stem cell differentiation include endodermal cells (Sox17 or AFP marker positive cells, etc.), mesodermal cell's (Brachyury, Flk1, Mox marker positive cells, etc.), and ectodermal cells. Examples of the ectodermal cells include neural cells (NCAM, TuJ1, tyrosine hydroxylase (TH), serotonin, nestin, MAP2, MAP2ab, NeuN, GABA, glutamate, ChAT, or Sox1 marker positive cells, etc.), epidermal cells (cytokeratin marker positive cells, etc.), sensory cells (RPE or rhodopsin marker positive cells, etc.), pigmentary cells (TRP-1 marker positive cells, etc.), and neural crest-derived mesenchymal cells (SMA marker positive cells, etc.). The SFEB method (see Nature Neuroscience 8, 288-296, 2005; International Publication No. 2005/123902) can be used to preferably induce nervous system cells, such as neural cells (e.g. cerebral neural cells) and their precursors, from the ES cells. In this case, factors can be used as follows; Nodal inhibitors (Lefty-A, Lefty-B, Lefty-1, Lefty-2, soluble Nodal receptors, Nodal antibodies; Nodal receptor inhibitors, etc.); Wnt inhibitors (Dkk1, Cerberus proteins, Wnt receptor inhibitors, soluble Wnt receptors, Wnt antibodies, casein kinase inhibitors, dominant negative Wnt proteins, etc.); and BMP inhibitors (anti-BMP antibodies, soluble BMP receptors, BMP receptor inhibitors, etc.). According to the methods of the present invention, the stem cells (for example, human ES cells) can be efficiently differentiated into specified cells. The methods of the present invention have further advantages in that it can be preferably used in other methods (for example, a SDIA method, a AMED method, a method using PA6 cells), which enable the stem cells to be differentiated into neural cells (forebrain neural cells and/or cerebral dorsal (cortical region) cells and cerebral ventral (basal ganglion region) cells).

The present invention provides a cell preparation obtained by the methods of the present invention and/or the above-mentioned dissociation treatments. The cell preparation of the present invention preferably includes a stem cell and a ROCK inhibitor. A cell preparation of the present invention can be a preparation comprising dissociated cells such as small cell aggregates composed of a plurality of single cells. Conventionally, the survival rate of human ES cells subjected to dissociation treatment was extremely low, however, such a cell preparation can improve the survival rate or differentiation efficiency of the stem cells such as ES cells, preferably human or neural stem cells, again preferably human. The cell preparation of the present invention, for example, can be used for the storage (for example, cryopreservation) and/or transport of stem cells or the subculture of stem cells. When the cell preparation is used for the cryopreservation of stem cells, the cell preparation of the present invention can further include the above described serum or substitute thereof, or an organic solvent (for example, DMSO). In this case, the concentration of serum or substitute thereof can be, but is not limited to, about 1-50% (v/v), preferably about 5-20% (v/v). The concentration of organic solvent can be, but is not limited to, about 0-50% (v/v), preferably about 5-20% (v/v). Compositions of these embodiments of the invention can include serum or can be serum free and separately can include feeder cells.

The present invention provides a culture agent of stem cells comprising a ROCK inhibitor. Generally, the culture agent will be a culture medium for stem cells. The culture agent of the present invention can be preferably used in the culture methods of the present invention.

The present invention also provides a combination comprising a ROCK inhibitor and other components. For example, the combination of the present invention can be used for culturing of stem cells (for example, passage culture, differentiation induction culture).

For example, the combination of the present invention may be a composition. The composition of the present invention can be provided in the form of a mixture of a ROCK inhibitor and other components. The other components which can be included in the composition of the present invention include, for example: differentiation adjustment agents of stem cells such as differentiation inhibitors of stem cells (for example, serum, FGF, LIF, BMP, Wnt, an extracellular matrix, TGF-β, a feeder cell), and differentiation inducers of stem cells (for example, a BMP inhibitor, a Wnt inhibitor, a Nodal inhibitor, retinoic acid, serum, an extracellular matrix, the feeder cells such as mesenchymal cells); as well as the culture additive (for example, KSR, 2-mercaptoethanol, amino acids, fatty acids and the other factors described above).

The combination of the present invention can also be a kit. The kits of the present invention can comprise a ROCK inhibitor and other components separately (i.e. a non-mixed manner). For example, the kit of the present invention can be provided in the form of the each component being packaged in a container individually. The other components which can be contained in the kit of the present invention include, for example: the other components mentioned above, which can be included in the composition of the present invention; a material for identification or measurement (detection or quantification) of stem cells or differentiated cells (for example, an antibody against the cell marker); a cell culture medium; a container for culturing which is treated with an extracellular matrix; a plasmid for genetic recombination and a selective agent thereof.

The present invention also provides a culture system wherein stem cells and a ROCK inhibitor are contained in a medium. The culture system of the present invention can contain stem cells in the medium of the present invention. The culture system of the present invention can further contain cell culture factors in a medium, other than the components described in detail in relation to the methods of the present invention, such as a feeder cell, cell a supporting matrix, a ROCK inhibitor.

The content of all publications, including patent and patent application specifications referenced in the present specification, are fully incorporated herein by reference for all purpose.

Figures 1L, 1M, 1N:
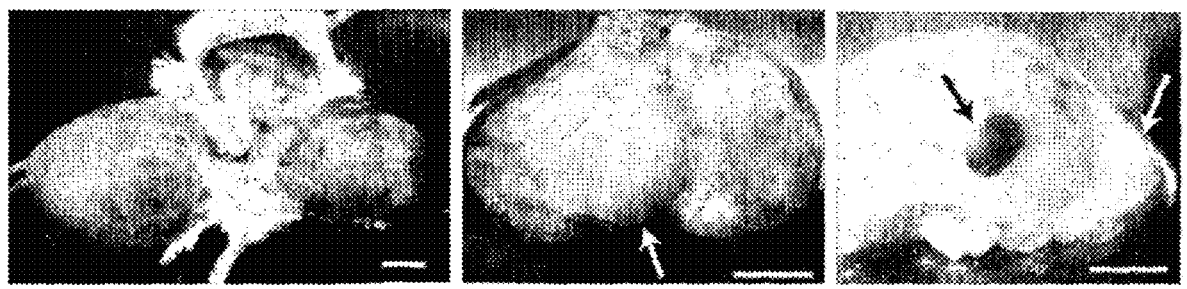

Detailed examples of the present invention are provided as follows, however the present invention is not limited to the following examples. The Examples are illustrated by the following drawings:

FIGS. 1A-1N—The ROCK inhibitor Y-27632 markedly increases the cloning efficiency of hES cells (KhES-1) without affecting their pluripotency. (FIGS. 1A-1C) Low-density culture of dissociated hES cells in the absence (FIG. 1A) and presence (FIG. 1B) of 10 μM Y-27632 on MEF for seven days. Almost all colonies were positive for ALP. Bars, 500 μm. (FIG. 1C) Ratios of ALP+ colonies to the number of initially seeded hES cells (**, P<0.01 vs control, n=3). (FIGS. 1D-1F Immunostaining of Y-27632-treated hES cell colonies with anti-E-cadherin (FIG. 1D), -Oct3/4 (FIG. 1E) and -SSEA-4 (FIG. 1F) antibodies. Bottom panels are nuclear DAPI staining. Bars, 100 μm. Y-27632 treatment did not cause a drastic change in actin-bundle formation of hES cells (not shown). (FIG. 1G) RT-PCR analysis of the early mesodermal markers Brachyury and Meox1 in differentiating hES cells. RT(−), G3PDH PCR without reverse transcription. (FIG. 1H) RT-PCR analysis of the early endodermal marker Sox17 in differentiating ES cells. (FIGS. 1I-1K) Immunostaining for the mesodermal and endodermal markers in differentiating hES cells on an 8-well chamber slide coated with collagen I and IV. (FIG. 1I) Expression of the mesodermal marker Brachyury (red) in a number of differentiating cells. DAPI was used for nuclear staining (blue; c). Bar, 10 μm. (FIG. 1J) Immunostaining of smooth muscle actin (SMA; red) in hES cell (Y-27632-treated)-derived cells cultured on OP9 cells for 12 days. Nuclei were stained with DAPI (blue). Bar, 5 μm. (FIG. 1K) Immunostaining of Hnf3β and E-cadherin in an hES cell-derived epithelial sheet on day 6. Bar, 5 μm. (FIGS. 1L-1N) Teratoma formation (100%, n=20) from hES cells maintained at low density in the presence of Y-27632 (30 passages). Bars, 1 cm. The cells were bilaterally injected into the SCID mouse testes (FIG. 1L). After 9 weeks, the teratomas contained a mixture of well-differentiated tissues including macroscopic cartilages (white arrows; FIG. 1M, FIG. 1N) and pigment epithelium (black arrow; FIG. 1N).

Figure 2A:
Figure 2B:
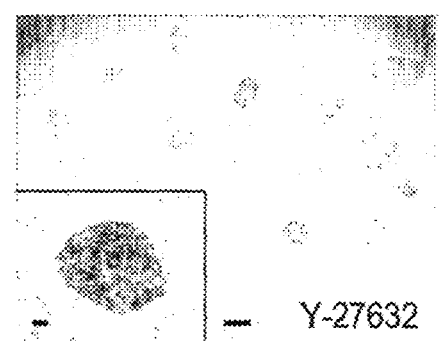
Figure 2C:
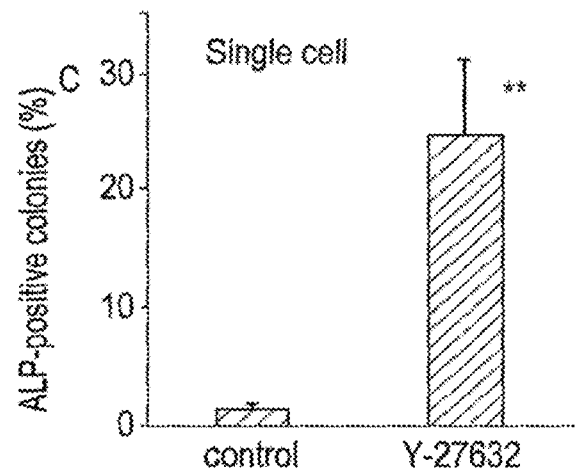
Figure 2D:
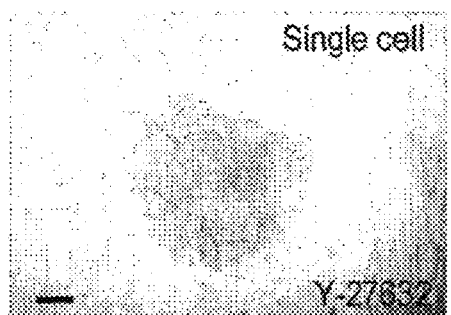
Figure 2E:
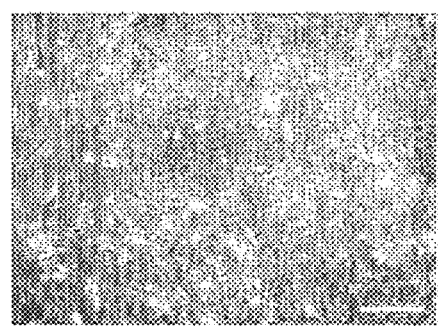
Figure 2F:
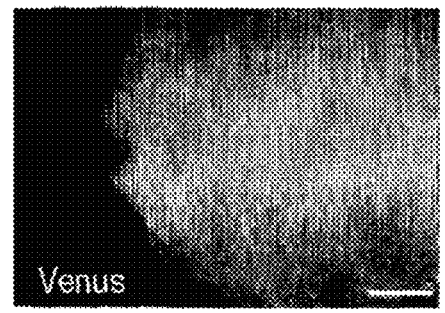
Figure 2G:
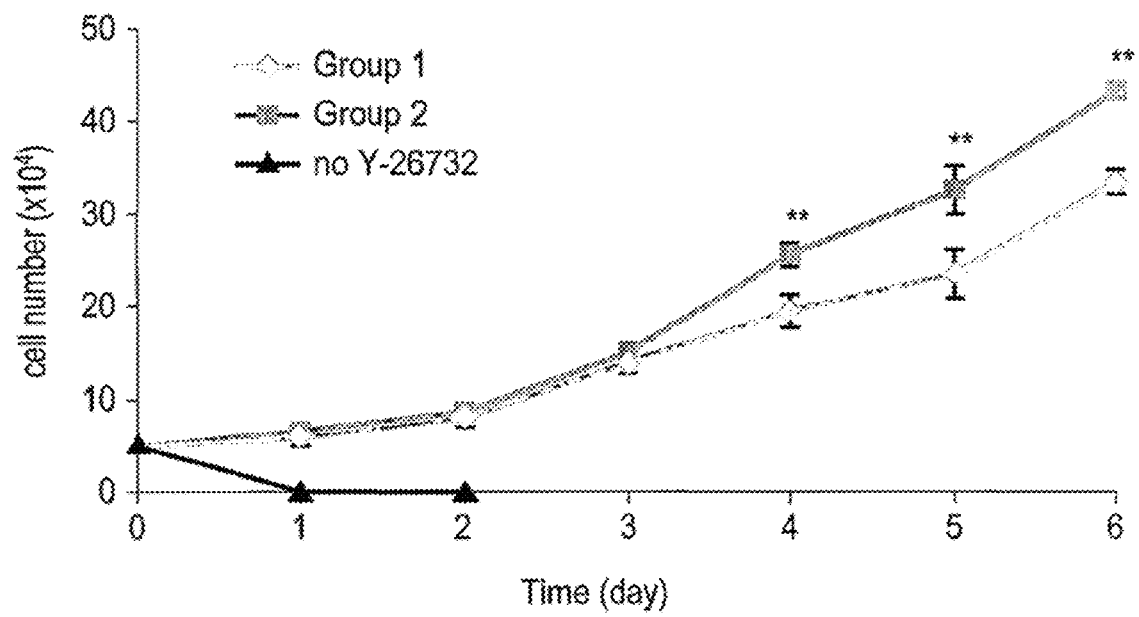
Figure 2H:
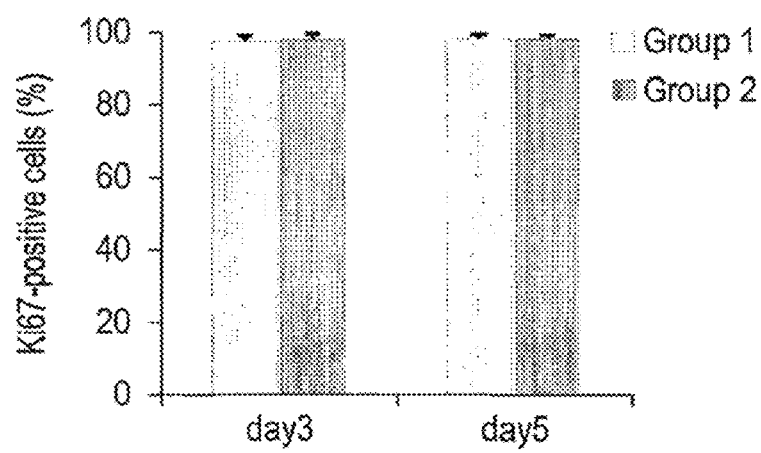
Figure 2I:
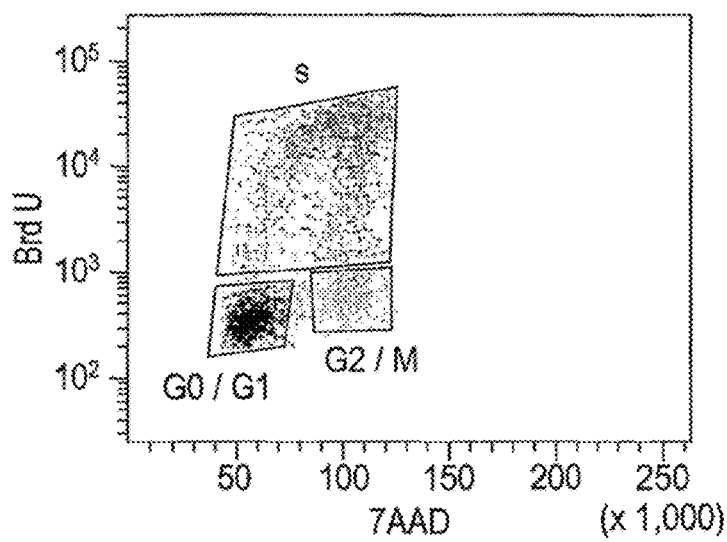
Figure 2J:
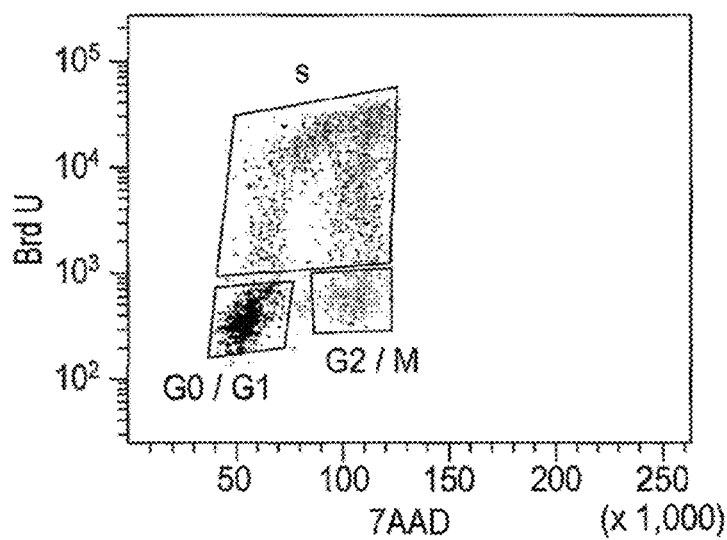
Figure 2K:
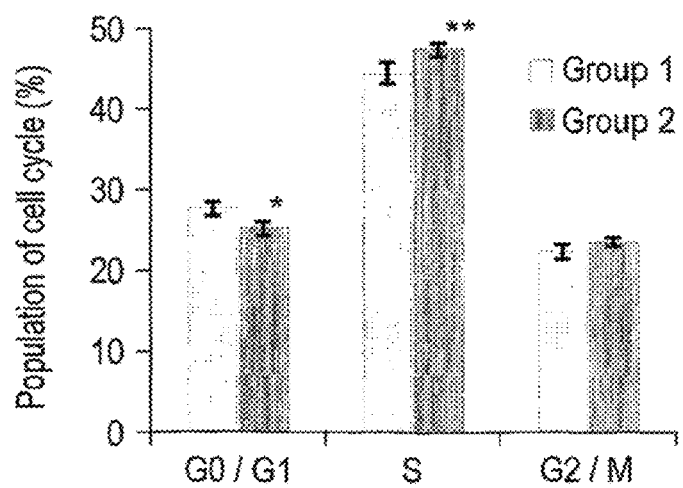
Figure 2L:
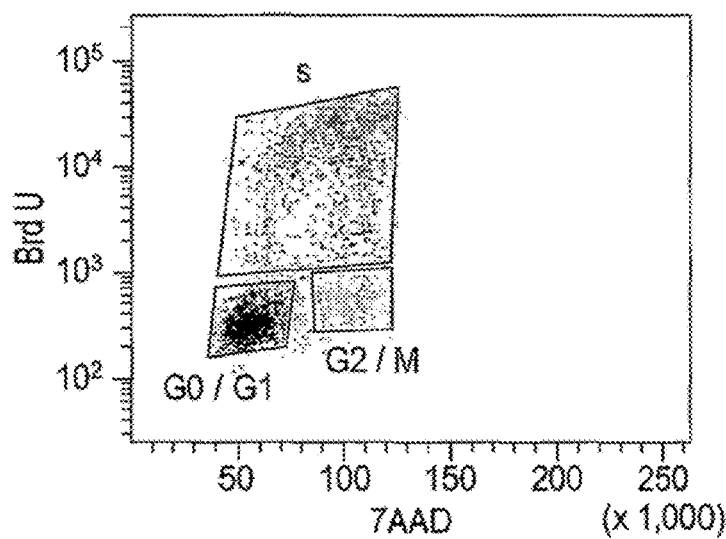
Figure 2M:
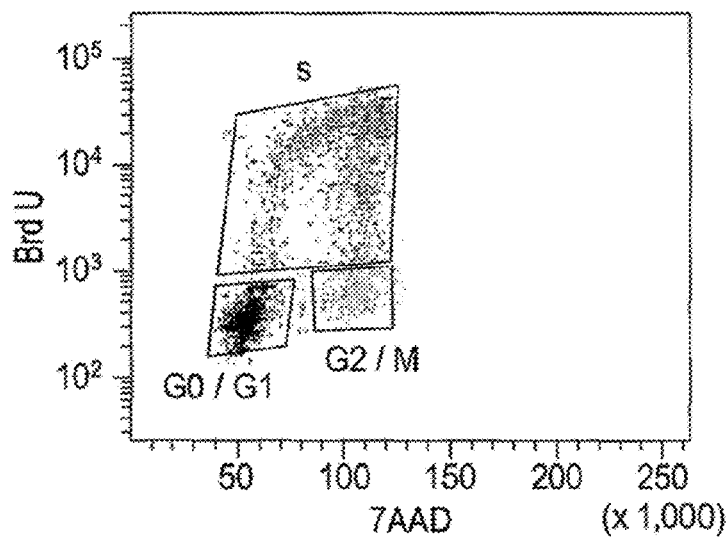
Figure 2N:
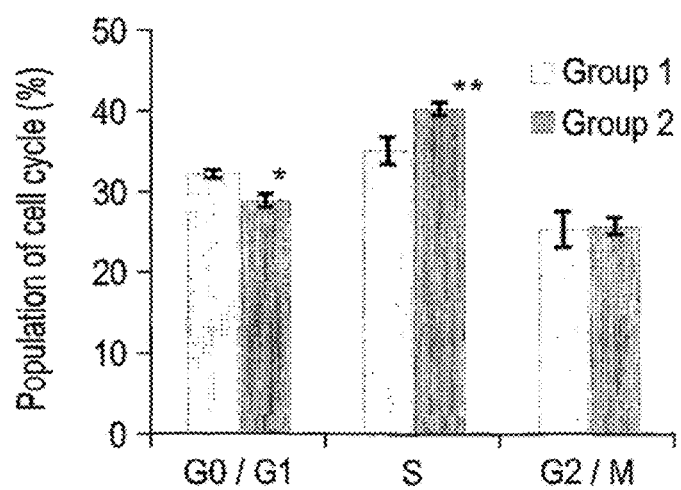

FIGS. 2A-2N—Y-27632 directly enhances the cloning efficiency of hES cells (KhES-1). (FIGS. 2A, 2B) Feeder cell-free culture of hES cells on matrigel-coated plates in MEF-conditioned medium. Bars, 500 μm. Colony formation from dissociated hES cells was clearly enhanced by Y-27632 (FIG. 2B; inset, a high magnification view of a typical colony; bar, 100 μm) whereas few colonies formed in its absence (FIG. 2A; <0.2% and 10.2±1.2% without and with Y-27632, respectively; P<0.001, n=3). (FIG. 2C, FIG. 2D) Culture of a single hES cell on MEF in each well of a 96-well plate in the presence of 10 μM Y-27632 for seven days. (FIG. 2C) Percentages of the presence of an ALP+ colony (FIG. 2D) in each well (, P<0.01 vs control, n=3 studies). Control, untreated cells. Bar, 100 μm. (FIG. 2E, FIG. 2F) Formation of hygromycin-resistant colonies from Y-27632-treated hES cells in low-density dissociation culture on MEF 12 days after transfection. Bars, 100 μm. (FIG. 2E) Phase-contrast view. (FIG. 2F) Venus-GFP expression. (FIG. 2G) Growth curve of hES cells cultured on MEF with different time courses of Y-27632 treatment. Group 1 (blue), Y-27632 treatment during the first 12 hours only (with one-hour pretreatment); Group 2 (red), continuous Y-27632 treatment during the entire culture period; No Y-27632, no Y-27632 treatment at all (purple). For each condition, $5\times10^4$ dissociated cells/well (6-well plate) were plated on MEF. , P<0.01, Group 2 vs Group 1 (n=3 studies). (FIG. 2H) Percentages of Ki67+(mitotic) cells in Nanog+ hES cells in Groups 1 (blue) and 2 (red) on days 3 and 5. (FIGS. 2I-2N) Flow-cytometric analysis of cell-cycle phase-specific populations. (FIG. 2I, FIG. 2J, FIG. 2L, FIG. 2M) Flow-cytometry patterns. X axis, DNA content shown by 7-AAD-binding; Y axis, BrdU uptake after a one-hour exposure. (FIG. 2K, FIG. 2N) Relative percentages of phase-specific populations among the hES cells in Groups 1 (blue) and 2 (red). (FIGS. 2I-2K) day 3. (FIGS. 2L-2N) day 5. *, P<0.05; **, P<0.01, Group 2 vs Group 1 (n=3 studies). The degree of increase in cell growth is not very large and cannot explain the robust increase of cloning efficiency (1% vs 27%).

Figure 3A:
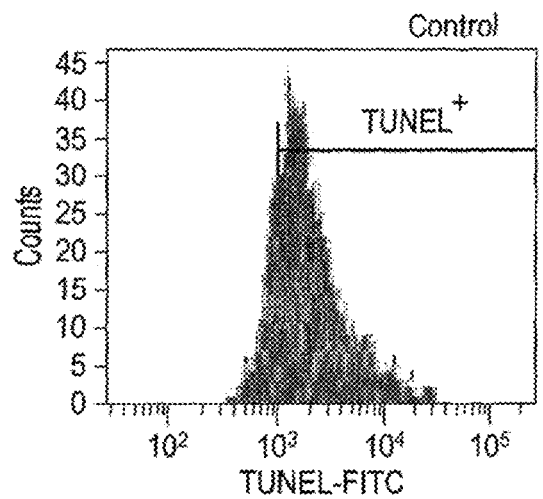
Figure 3B:
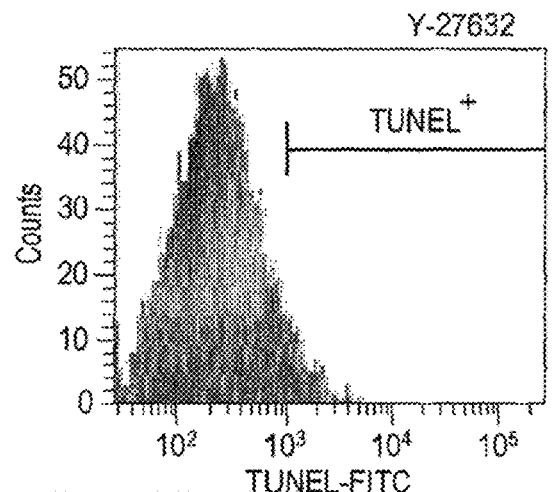
Figure 3C:
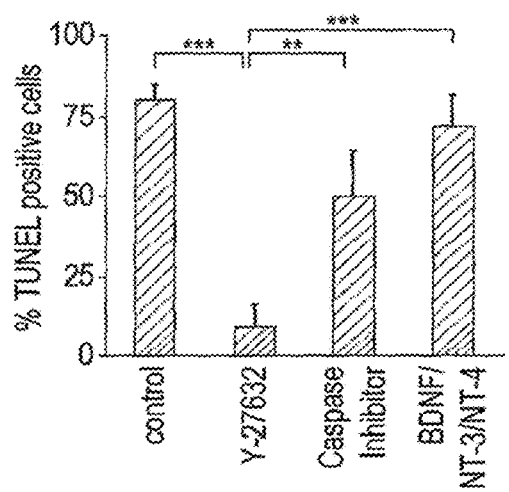
Figure 3D:
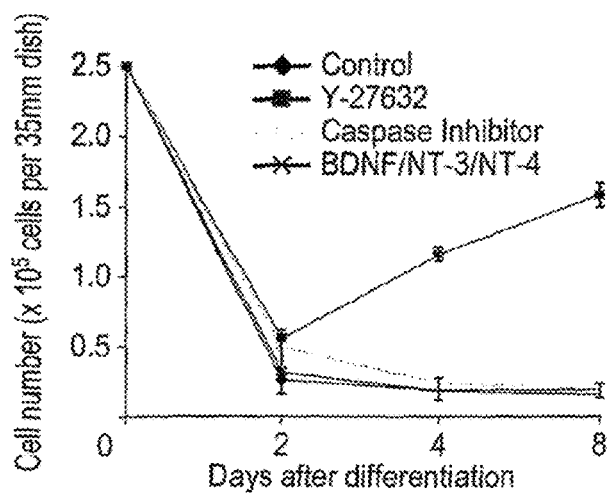
Figure 3E:
Figure 3F:
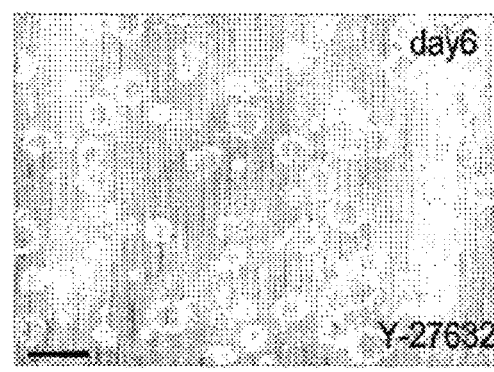
Figure 3G:
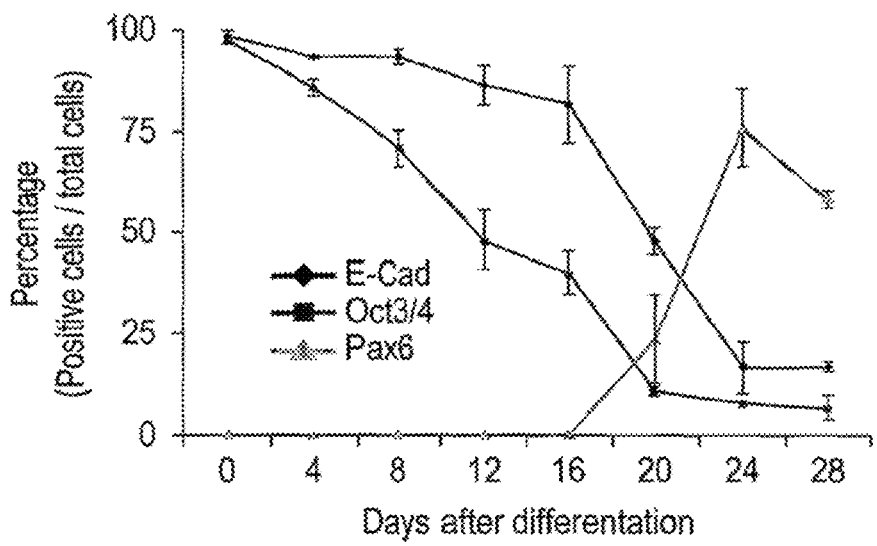
Figure 3H:
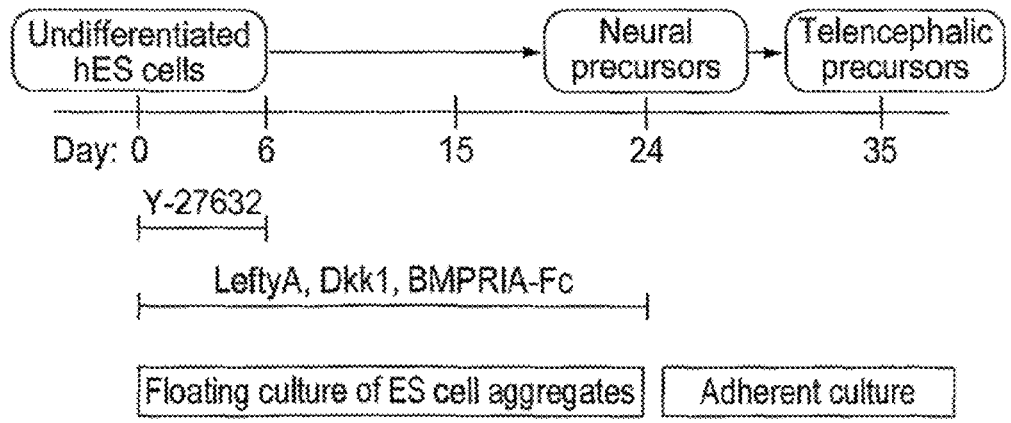
Figure 3I:
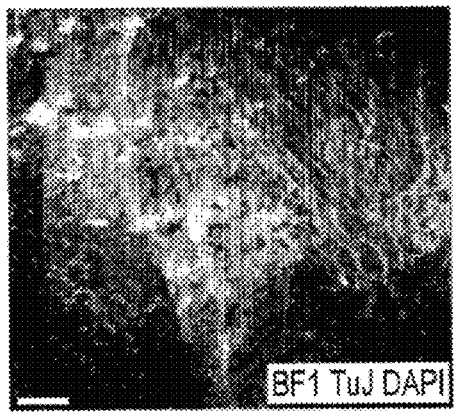
Figure 3J:
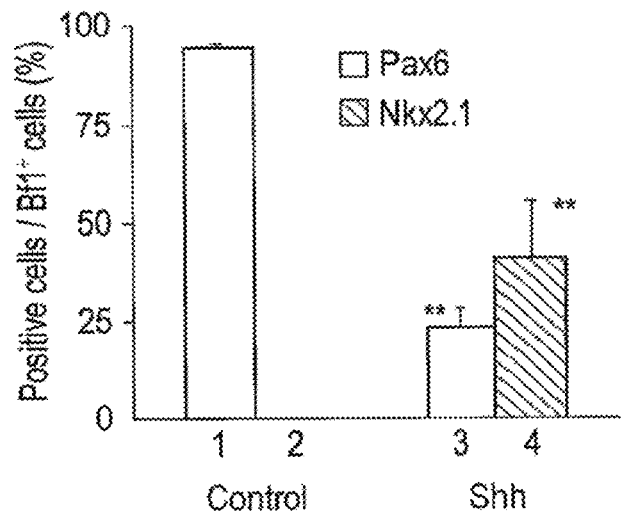
Figure 3K:
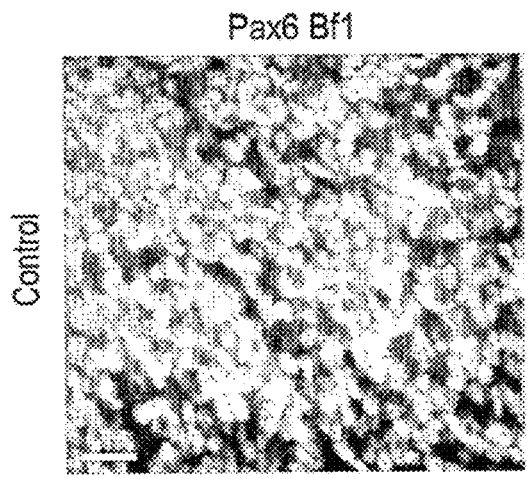
Figure 3L:
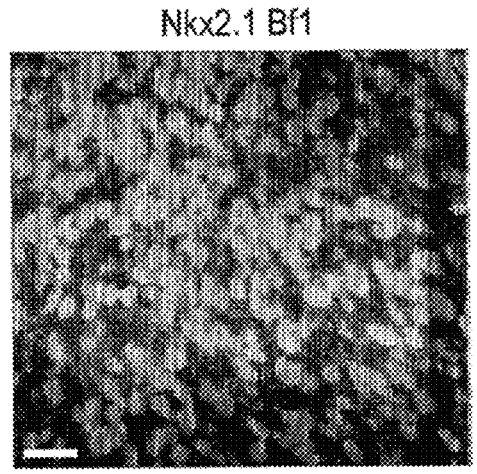
Figure 3M:
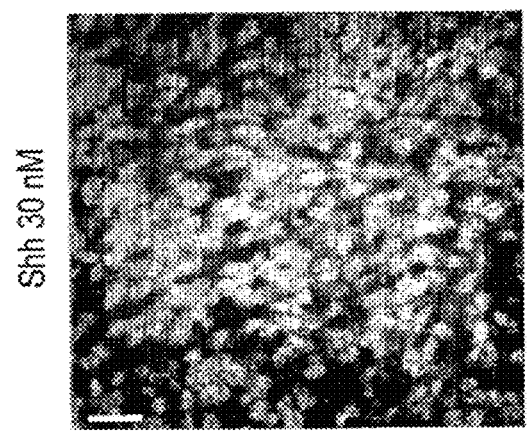
Figure 3N:
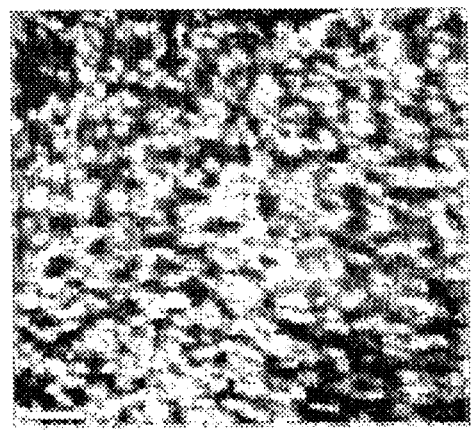

FIGS. 3A-3N—The ROCK inhibitor prevents apoptosis and promotes survival of dissociated hES cells (KhES-1) in suspension culture. (FIGS. 3A-3C) TUNEL assay. Dissociated hES cells were cultured in suspension for two days in the absence (FIG. 3A) or presence (FIG. 3B) of 10 μM Y-27632. TUNEL+ cells were analyzed by FACS. (FIG. 3C) Effects of Y-27632, Caspase inhibitor 1 (Z-VAD-fmk) and a neurotrophin cocktail (BDNF+NT-3 and -4) on percentages of apoptotic cells (, P<0.01; *, P<0.001, between each pair; n=3 studies). (FIGS. 3D-3F) Supportive effects of Y-27432 on hES cell survival/growth in suspension culture. (FIG. 3D) Cell numbers two, four and six days after culturing $2\times10^5$ dissociated hES cells in 35-mm plates (n=3). On day 6, efficient formation of cell aggregates was observed with the Y-27632-treated ES cells (FIG. 3F), but not with the control cells (FIG. 3E). Bars, 300 μm. (FIG. 3G) Time-course analysis of the expression of Pax6 (green), Oct3/4 (red) and E-cadherin (blue) in SFEB-h-cultured hES cells. (FIG. 3H) Schematic of the culture protocol. (FIG. 3I) Immunostaining of hES cell-derived neural cells induced in SFEB-h culture. Bf1 (red), TuJ1 (green), DAPI (blue). Bar, 50 μm. Note that some Bf1+ cells were positive for the neuronal marker TuJ1. (FIG. 3J-3N) Immunostaining analysis of SFEB-h-induced neural cells. Bars, 25 μm. (FIG. 3J) Percentages of Bf1+ telencephalic cells that were positive for Pax6 and Nkx2.1 (**, P<0.01 vs control; n=3). Immunocytochemistry of SFEB-h-induced neural cells cultured without (FIG. 3K, FIG. 3L) or with (FIG. 3M, FIG. 3N) Shh (30 nM). Bf1 (green; FIGS. 3K-3N), Pax6 (red; FIG. 3K, FIG. 3M) and Nkx2.1 (red; FIG. 3L, FIG. 3N).

Figure 4H:
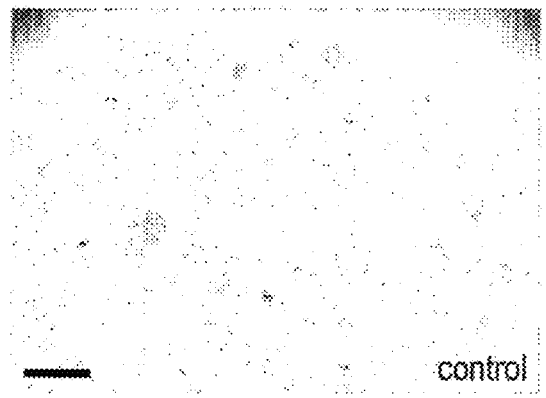
Figure 4I:
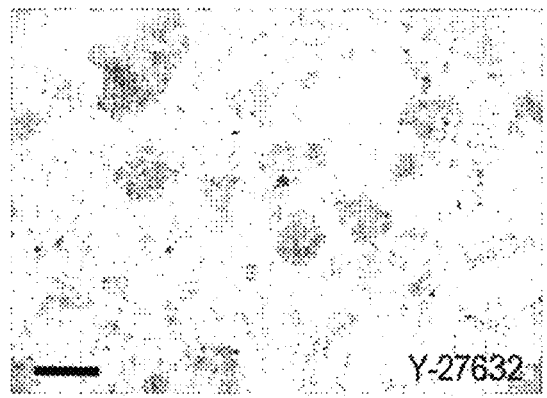
Figure 4J:
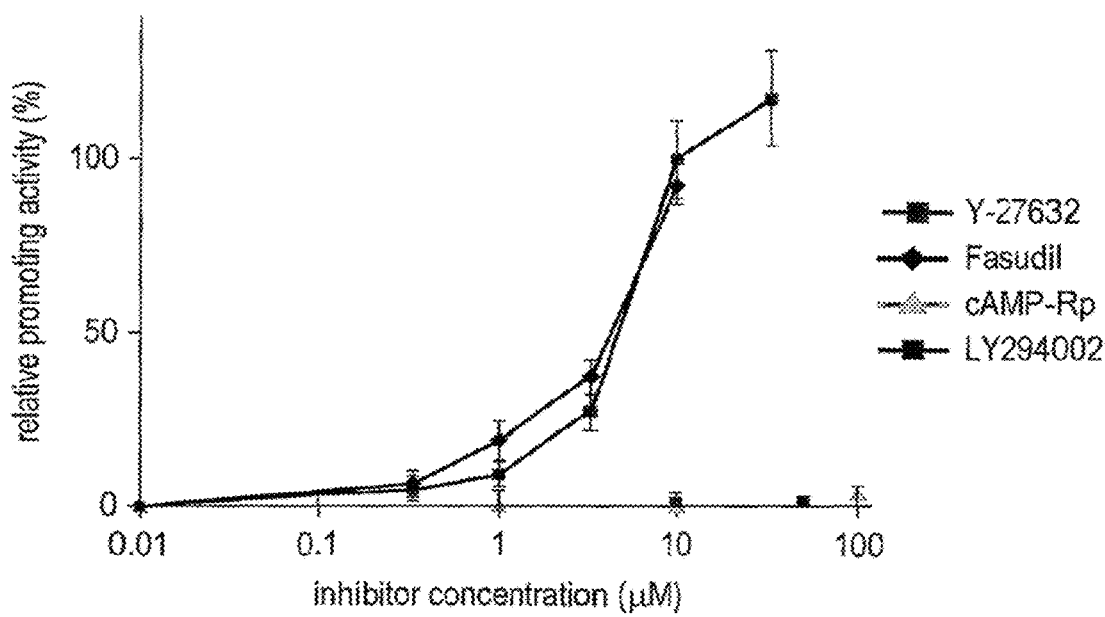
Figure 4K:
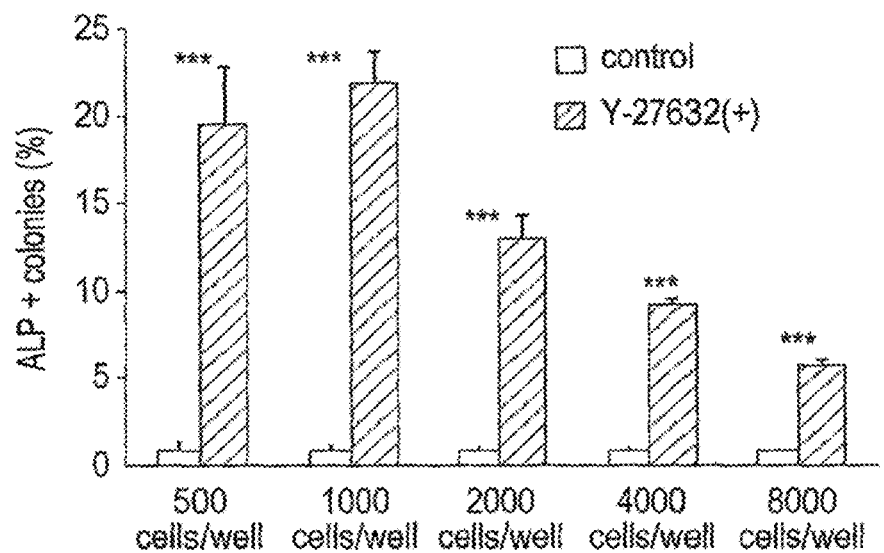
Figure 4L:
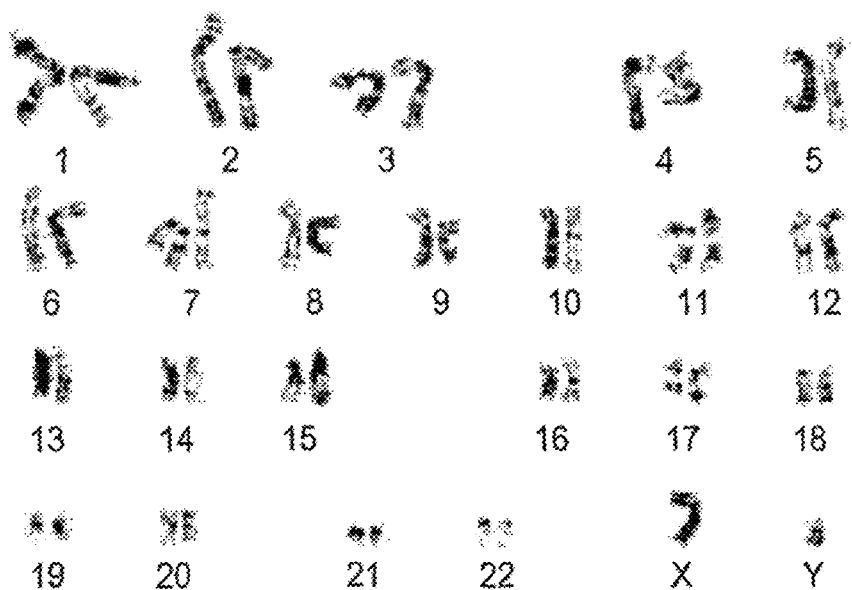

FIGS. 4A-4L—Analysis of hES cells cultured in the presence of Y-27632 at low density. (FIGS. 4A-4C) Immunostaining of E-cadherin (FIG. 4A), Oct3/4 (FIG. 4B) and SSEA-4 (FIG. 4C) in Y-27632-treated hES cells (KhES-1) after extended passaging (30 times) at low density with Y-27632 treatment. Lower panels show DAPI staining (blue). (FIGS. 4D-4G) Histological analysis (hematoxylin-eosin staining, 5 μM paraffin section) of teratoma tissues formed after subcapsular injection of hES cells (KhES-1) following extended passaging with Y-27632 into SCID mouse testes. (FIG. 4D) Cartilage, (FIG. 4E) neuroepithelium, (FIG. 4F) pigmented epithelium, and (g) gut-like mucosa with columnar epithelium. (FIG. 4H, FIG. 4I) After extended passaging involving low-density culture with Y-27632 treatment, efficient colony formation from dissociated hES cells (32.5±11%; KhES-1) remained dependent on Y-27632 (FIG. 4I) and few colonies were seen without it (FIG. 4H). (FIG. 4J) Dose-response relationship of two selective ROCK inhibitors (Y-27632, Fasudil; the cloning efficiency was 1.3±0.8% and 25.1±1.6% without and with 10 μM Fasudil; P<0.001, n=3) and two unrelated kinase inhibitors (cAMP-Rp, LY294002) on colony formation (KhES-1). Y-axis, ratios of promoting activity of colony formation to that with 10 μM Y-27632. (FIG. 4K) Enhancement of colony formation by Y-27632 at different plating densities of hES cells. ***, P<0.001 vs control (no treatment), n=5. (FIG. 4L) G-banding analysis (at 300-500 band levels) of hES cells (KhES-3) showing a normal karyotype (100%, n=5) after extended maintenance passaging with Y-27632 treatment for three months.

Figure 5A:
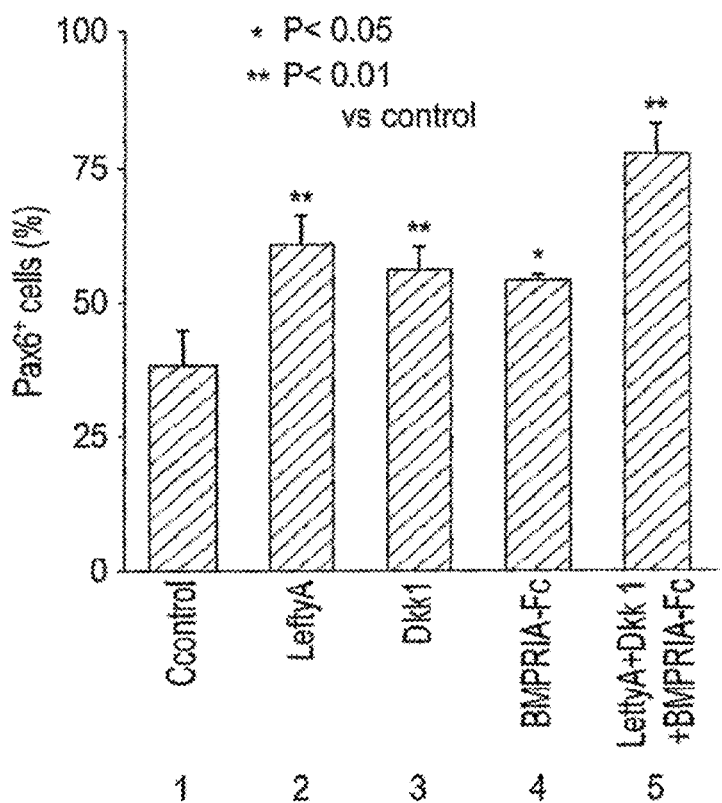
Figures 5B, 5C:
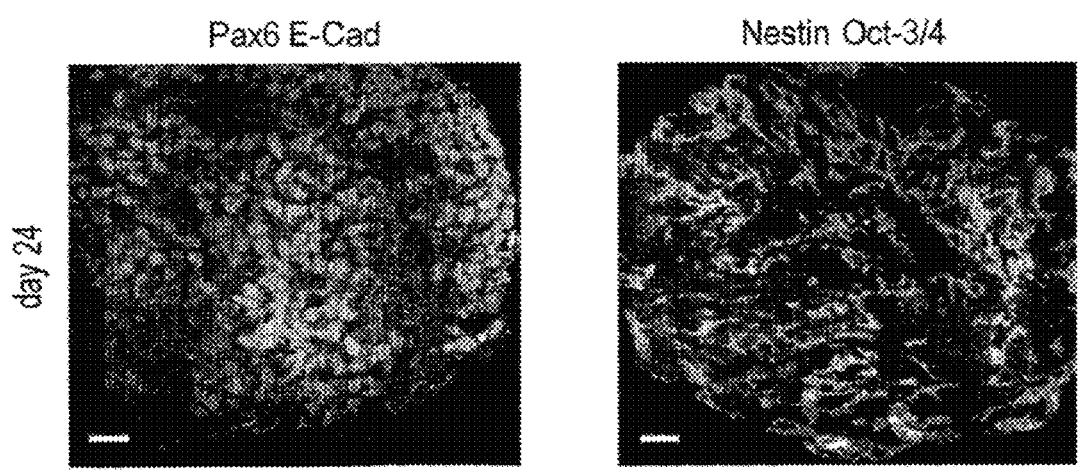

FIGS. 5A-5C Neural differentiation of hES cells (KhES-1) in suspension culture involving dissociation/reaggregation in the presence of Y-27632. (FIG. 5A) Effects of inhibitors of Nodal (5 μg/ml Lefty, lane 2), Wnt (500 ng/ml Dkk1, lane 3) and BMP (1.5 μg/ml BMPR1A-Fc, lane 4) on hES cell differentiation into Pax6+ neural progenitors. Lane 5, combination of the three factors (*, P<0.05; **, P<0.01 vs control; n=3 studies). (FIG. 5B, FIG. 5C) Immunostaining of SFEB aggregates of hES cells (day 24) cultured with Y-27632 (days 0-6) and the three inhibitors (days 0-24; SFEB-h). (FIG. 5B) Pax6 (green) and E-cadherin (red). (FIG. 5C) Nestin (green) and Oct3/4 (red).

EXAMPLES

Example 1: Improvement in Cloning Efficiency of Human Embryonic Stem Cells by ROCK Inhibitor Y-27632

(Method)

The Human embryonic stem cells used for the experiments described herein were embryonic stem cells (KhES-1, KhES-2 and KhES-3) from human blastocysts established in the laboratory of Norio Nakatsuji, at the Institute for Frontier Medical Sciences, Kyoto University, which were distributed and used (mainly KhES-1) following the human embryonic stem cell guidelines of the Japanese government. In accordance with the method of the Nakatsuji laboratory (Suemori et al., Biochem Biophys Res Commun. 345, 926-32 (2006)), undifferentiated human embryonic stem cells were cultured on a plastic culture dish with mouse embryonic fibroblasts (inactivated with mitomycin, MEF) seeded as a feeder layer of cells. More specifically, the culture medium containing comprising KSR (Invitrogen/Gibco-BRL) at the final concentration of 20%, 1×NEAA (non-essential amino acids, Invitrogen/Gibco BRL), 2 mM L-giutaminic acid and 0.1 mM 2-mercaptoethanol in D-MEM F12 (Sigma D6421) was used, and the culturing was performed at 37° C., 5% $CO_2$. Passaging was performed in every three or four days, and the embryonic stem cells were detached from the feeder layer using the dissociation liquid (containing 0.25% trypsin, 1 mg/ml collagenase IV solution, 1 mM $CaCl_2$ in a phosphate buffered saline; all of which from Invitrogen/Gibco-BRL), followed by dissociated into small cell clumps (of about 50-100 cells) by pipetting, and then were seeded on the feeder layer which had been formed from seeding MEF on the day before.

The cell death inhibiting effect and the influence on cloning efficiency, of ROCK inhibitor, for the human embryonic stem cell culture after dissociation to single cells were examined as follows. The human embryonic stem cells as cultured above were detached from the feeder layer as small cell clumps, and further contaminating feeder cells were adhered to the bottom of a cellular adhesive culture plate (0.1% gelatine coated) for removing, by incubating in the maintenance culture medium at 37° C. for one hour, wherein the embryonic stem cell clumps do not strongly adhere to the plate while the contaminating feeder cells strongly adhere. The embryonic stem cell clumps ware dissociated to single cells by trypsin digestion (0.25% trypsin—EDTA, at 37° C. for 5 minutes), and seeded on a MEF feeder layer in 96 well culture plates at low density (500 cells/0.32 $cm^2$ in 0.15 ml of medium). The number of formed colonies was counted six days after culture in the maintenance culture medium. ROCK inhibitor Y-27632 was added at the concentration of 10 μM one hour prior to detaching the cells from the feeder layer, and the same amount was added to culture in the same amount after the detachment.

Also, to evaluate whether promotion of cloning would be caused by the autocrine factor of human embryonic stem cell, a similar experiment was performed in 96 well culture plates at clonal density (one cell per well) of human embryonic stem cells, and the cloning efficiency was determined.

(Result)

After six days culture the cloning efficiencies (ratios of the numbers of formed colonies to the initial numbers of human embryonic stem cell seeded) were 1% and 27% without and with the ROCK inhibitor, respectively. The cells in colonies formed by the treatment with the ROCK inhibitor expressed alkaline phosphatase and Oct3/4, which are markers for undifferentiated embryonic stem cells. The superior effect of the ROCK inhibitor for cloning efficiency was confirmed not only in KhES-1 but also KhES-2 and KhES-3 as human embryonic stem cells.

Also, using 96 well plates at clonal density (one cell per well) of human embryonic stem cells, the cloning efficiencies were under 1% and 25% without and with the ROCK inhibitor, respectively. Thus, it was considered that the superior effect of the ROCK inhibitor for cloning efficiency was not due to an autocrine factor of human embryonic stem cell.

Accordingly, it was found that ROCK inhibitor Y-27632 significantly improved the survival rate of human embryonic stem cells.

Example 2: Activation of Rho in Dissociated Human Embryonic Stem Cells (Method)

The maintenance culture of human embryonic stem cells was performed by passages of small cell clumps as described in Example 1.

As described in Example 1, human embryonic stem cells were dissociated to single cells by trypsin digestion, suspended in the culture medium for maintenance culture, and incubated at 37° C. The cells were collected by centrifugation after 0 minutes, 15 minutes, 30 minutes, 60 minutes, 120 minutes of the incubation, and subsequently treated with The small GTPase activation kit (Cytoskeleton company, Denver, CO) following the manufacturer's instruction, and analyzed by Pull down method. Activation of Rho was judged on the basis of increases in the ratio of activated Rho (GTP associated Rho) to total Rho by Western blotting. A sample of cells was prepared from a 10 cm culture plate (about $1 \times 10^6$ cells) as a batch.

(Result)

Remarkable activation of Rho was seen 15-30 minutes after the dissociation/incubation of human embryonic stem cells.

The activation of Rho was decreasing slowly over 30 minutes.

Accordingly, the results indicate that the superior effect of Y-27632 to human embryonic stem cells was due to the inhibition of the Rho activation, which was caused by the ROCK inhibition action of Y-27632.

Example 3: The Colony Formation Efficiency of Human Embryonic Stem Cells in the Maintenance Culture by Different Kinase Inhibitors (Method)

The effects of other ROCK inhibitors on the cloning efficiency of human embryonic stem cells in maintenance culture were evaluated using methods as described in example 1. The ROCK inhibitors, Fasudil/HA1077 (10 μM) and H-1152 (200 nM) were used. Also, inhibitors for other kinases were used for reference. The inhibitors for other kinases used were: cAMP-Rp (1-100 μM) and KT5720 (5-500 nM), which are protein kinase A inhibitors; bisindolylmaleimide (0.01-5 μM) and staurosporine (1-50 nM), which are protein kinase C inhibitors; PD98059 (0.5-50 μM), which is an MAPK inhibitor; LY294002 (1-50 μM), which is a PI3K inhibitor; and ML-7 (0.3-30 μM), which is an MLCK inhibitor.

(Result)

In the cases of ROCK inhibitors (Fasudil/HA1077 and H-1152), significant enhanced cloning efficiencies were observed compared to without the inhibitors, however in the cases of inhibitors for other kinases, no enhancement was observed.

Accordingly, it was found that ROCK inhibitor could specifically improve the survival rate of human embryonic stem cells.

Example 4: Suppression of Apoptosis by the ROCK Inhibitor in Suspension Culture of Dissociated/Reaggregated Human ES Cells (Method)

Human ES cells subjected to maintenance culture were detached as small cell clumps (aggregates) from feeder cells in the same manner as in Example 1, and after removal of residual feeder cells, they were dissociated into single cells by trypsin digestion. After centrifugation, $2 \times 10^5$ cells were dissociated in serum-free culture medium for post differentiation induction (Watanabe et al., Nature Neuroscience 8, 288-296, 2005; supplemented with G-MEM, KSR and 2-mercaptoethanol, KSR was added at a concentration of 20%). The singly-dissociated human ES cells ($1.0 \times 10^5$ cells/ml) were suspension-cultured in a non-cell adhesive 35 mm culture plate to form aggregates, and were cultured in the same culture medium for 2-6 days (SFEB method; See the above reference of Watanabe et al.). After 2-day culture, the percentage of apoptic cells was measured by TUNEL method (MEBSTAIN Apoptosis kit Direct, MBL). Treatment with ROCK inhibitor, Y-27632, was initiated at 1 hour before cell separation in the same manner as in Example 1, and the inhibitor was added to maintenance culture medium also after dissociation. For comparison, caspase inhibitor (ZVAD; 10 μM) and BDNF/NT-3/NT-4 (mixture of 50 ng/ml each), whose apoptosis suppressive effect has been reported, were used to conduct the experiment. In addition, the number of surviving cells on day 6 was counted in each case.

(Result)

In the non-supplemented control, after 2-day culture, apoptosis was observed in 80% of cells by TUNEL method. In cells treated with ROCK inhibitor, only 9% of cells were TUNEL-positive. On the other hand, supplementation of caspase inhibitor (ZVAD; 10 μM) and BDNF/NT-3/NT-4 (50 ng/ml each) resulted in 72% and 69% TUNEL-positive cells, respectively. These results indicate strong cell death suppressive activity of ROCK inhibitor. Accordingly, as for the number of surviving cells on day 6, 8% survived in the non-supplemented group at the start of dissociation culture, while 70% survived in the group treated with ROCK inhibitor; more cells survived. The surviving cells, treated with either caspase inhibitor or BDNF/NT-3/NT-4, accounted for less than 10% of the plated cells.

As described above, it was demonstrated that ROCK inhibitor markedly improved the survival rate of human ES cells.

Example 5: Differentiation Induction into Neuronal Precursor Cells and Brain Precursor Cells by SFEB Method Using Singly-Dissociated Human ES Cells (Method)

Human ES cells subjected to maintenance culture were detached from feeder cells as small cell clumps in the same manner as in Example 4, and after removal of residual feeder cells, they were dissociated into single cells by trypsin digestion. After centrifugation, cells were dissociated into culture medium for differentiation induction at $2 \times 10^5$ cells/mL, and were suspension-cultured using a non-cell adhesive culture plate to conduct serum-free culture (SFEB method) of suspended aggregates. In addition, Nodal inhibitor LeftyA (1 μg/ml, R&D), Wnt inhibitor Dkk1 (500 ng/ml, R&D) and BMP inhibitor BMPR1A-Fc (1.5 μg/ml, R&D) were added for the first 10 days after the start of culture for differentiation induction. After serum-free suspension culture for 16-35 days, the cell aggregates were fixed and immunostained by fluorescence antibody method. Treatment with the ROCK inhibitor, Y-27632, was initiated at 1 hour before cell separation in the same manner as in Example 1, and the inhibitor was added to maintenance culture medium for the first six days also after dissociation.

For the differentiation into brain precursor cells, on day 25 of SFEB culture, floating cell aggregates were transferred into a poly-D-lysine/laminin/fibronectin-coated culture slide, and were cultured in an adhesion state for additional 10 days. In the adhesion culture, Neurobasal medium, supplemented with B27 (vitamin A-free) and 2 mM L-glutamine (both supplied by Gibco-BRL), was used as a culture medium.

(Result)

On day 20 after the start of differentiation culture, in almost all the cell aggregates treated with the ROCK inhibitor, cells positive for neuronal precursor cell markers, nestin and Pax6, were expressed. On day 24 of differentiation culture, the number of these positive cells increased, and about 80% of cells turned into Pax6-positive cells. On the other hand, undifferentiated-state ES cell marker, Oct3/4 positive cells accounted for less than 10%. On day 35 of differentiation culture, there were many brain precursor marker, Bf1 positive cells in about 60% cell aggregates. This indicates that human ES cells generate cerebral nervous tissues. Without ROCK inhibitor treatment, there were few surviving cells on day 7 of differentiation culture.

In cells untreated with the ROCK inhibitor, few survived for 7 days or longer, and no significant formation of floating cell aggregates was observed.

Thus, it was found that the ROCK inhibitor did not impair the differentiation potency of human ES cells, and human cells treated with the ROCK inhibitor could very efficiently differentiate.

Example 6: Culture of Singly-Dissociated Human ES Cells by Feeder-Free Culture Supplemented with the ROCK Inhibitor (Method)

To demonstrate whether ROCK inhibitor treatment allows single dissociation culture of human ES cells also by feeder-free culture without using feeder cells such as mouse embryonic fibroblast (MEF), human ES cells were cultured on extracellular matrix prepared with MEF according to the known method by literature (Xu C—H et al., Nature Biotechnol., 19, 971-974 (2001)). Specifically, according to the above literature, MEF cells cultured to confluency were lysed on a culture dish by deoxycholate method to leave only extracellular matrix. Singly-dissociated human ES cells (500 cells/well of a 96-well plate) were seeded onto them under Y-2763 treatment (10 µM or 0 µM) by the same method as for the routine culture on MEF cells (abovementioned Example). Conditioned medium, in which human ES cell maintenance medium and MEF were preliminarily cultured for one day, was used as a culture medium. The number of human ES cell colonies formed 5 days later were counted.

(Result)

High cloning efficiency (10.2%) per seeded human ES cell was observed in the Y-27632-treated group. On the other hand, the cloning efficiency in the Y-27632-untreated group was less than 0.2%. The colonies formed in the Y-27632-treated group were strongly positive for undifferentiated-state marker, alkaline phosphatase. These findings indicate that the ROCK inhibitor had an effect not on feeder cells but directly on human ES cells to promote colony formation. In addition, even without using co-culture with feeder cells, it was demonstrated that the ROCK inhibitor allowed single dissociation culture of human ES cells when they are cultured on adequately-prepared extracellular matrix in the presence of liquid factors (e.g., factors contained in the conditioned medium).

Example 7: Maintenance Culture of Singly-Dissociated Human ES Cells by Short-Term ROCK Inhibitor Treatment (Method)

As for the maintenance culture of singly-dissociated human ES cells, in order to examine whether Y-27632 promotes cell survival at the early phase of dissociation culture, Y-27632 treatment time was divided into the following three groups to compare cell survival-promoting effects in maintenance culture.

Group 1: Y-27632 treatment (10 µM, same below) was conducted as 1 hour-pretreatment and only for the first 12 hours of culture after dissociation in the process of dissociation culture of human ES cells.

Group 2: Y-27632 treatment was conducted as 1 hour-pretreatment and for the entire culture period after dissociation in the process of dissociation culture of human ES cells.

Group 3: No Y-27632 treatment was conducted.

In these groups, surviving cells on day 3 per seeded cells ($5 \times 10^4$ cells per one well of a 6-well plate) were counted in maintenance culture system on MEF layer.

(Result)

In Group 3 untreated with Y-27632, no more than 1% of the total cells seeded survived on day 3. In Group 1 treated with Y-27632 for 12 hours after dissociation, 270% of the seeded cells were counted; in Group 2 treated with Y-27632 continuously, 290% of the seeded cells were counted. These results indicate that Y-27632 treatment has sufficiently high promoting effect in first half day after the start of dissociation culture in maintenance culture of human ES cells by adhesion culture.

Example 8: Cell Growth-Promoting Activity by ROCK Inhibitor Treatment in Maintenance Culture of Human ES Cells (Method)

In the same experiment as in the above Example 7, the effect of Y-27632 on the cell growth for 6 days after the start of dissociation culture was examined in Groups 1 and 2 by extending the culture period to 6 days.

(Result)

The number of cells on day 6 increased to 670% and 860% of the number of initially seeded cells in Groups 1 and 2, respectively. The population doubling time, based upon the number of cells during days 2 to 6 after the start of dissociation culture, was 49.0 hours for Group 1, and 41.5 hours for Group 2; the doubling time was shortened in half for Group 2. In both Groups 1 and 2, the percentage of apoptosis (the percentage of active Caspase 3-positive cells) on days 3 and 5 was less than 1% of total cells. These results indicate that, in addition to cell survival-supporting activity immediately after the start of dissociation culture, Y-27632 has cell growth-promoting activity on the survival cells thereafter.

Thus, stem cells are cultured in the presence of a ROCK inhibitor and the invention provides culture methods and media therefor.

REFERENCES

WO 2005/123902
Watanabe et al., Nature Neuroscience 8, 288-296 (2005)
Frisch et at, Curr. Opin. Cell Biol. 13, 555-562 (2001)
Riento et al., Nat. Rev. Mol. Cell. Biol. 4, 446-456 (2003)
Ishizaki et al., Mol. Pharmacol. 57, 976-983 (2000)
Narumiya et al., Methods Enzymol. 325, 273-284 (2000)
Minambres et al., J. Cell Sci. 119, 271-282 (2006)
Kobayashi et at, J. Neurosci. 24, 3480-3488 (2004)
Rattan et al., J. Neurosci Res. 83, 243-255 (2006)
Svoboda et al., Dev Dyn. 229, 579-590 (2004)

The invention claimed is:

1. A method of improving the differentiation efficacy of human pluripotent stem cells to ectodermal cells, which comprises culturing human pluripotent stem cells, which are dissociated single cells, in a serum-free culture medium which is suitable for induction of differentiation of pluripotent stem cells into ectodermal cells by a Serum-free Floating culture of Embryoid Body-like aggregates (SFEB) method, wherein the culture medium comprises a Rho kinase (ROCK) inhibitor for at least 2 days, wherein, during culturing, induction of differentiation occurs, and wherein the ectodermal cells are neural cells, or neural precursor cells.

2. The method according to claim 1, wherein the ROCK inhibitor is present in a culture medium in contact with the cells during a portion of the period of inducing differentiation to ectodermal cells.

3. The method according to claim 1, wherein the ectodermal cells are Nestin and Pax6 positive cells.

4. The method according to claim 1, wherein the induction of differentiation comprises inducing neural cells or neural precursor cells in the presence of a factor selected from the group consisting of Nodal inhibitors, Wnt inhibitors, and BMP inhibitors.

5. The method according to claim 1, wherein the ROCK inhibitor is Y-27632, Fasudil, or H-1152.

6. The method according to claim 1, wherein the human pluripotent stem cells are human embryonic stem cells.

7. The method according to claim 1, wherein prior to the culturing of the human pluripotent stem cells, which are dissociated single cells, in a serum-free culture medium, the pluripotent stem cells are cultured in a culture medium in the presence of the ROCK inhibitor and serum, serum extract, and/or feeders.

8. The method according to claim 1, wherein the ROCK inhibitor is present in a culture medium for up to six days.

9. The method according to claim 1, wherein after differentiation to neural cells or neural precursor cells is induced, the ROCK inhibitor is withdrawn from the culture medium.

10. The method according to claim 1, further comprising the step of dissociating human pluripotent stem cells into single cells prior to the step of culturing the dissociated human pluripotent stem cells in a serum-free culture medium.

11. The method according to claim 10, wherein the ROCK inhibitor is Y-27632, Fasudil, or H-1152.

12. The method according to claim 10, wherein the human pluripotent stem cells are human embryonic stem cells.

13. The method according to claim 10, wherein prior to the culturing of the human pluripotent stem cells, which are dissociated single cells, in a serum-free culture medium, the pluripotent stem cells are cultured in a culture medium in the presence of the ROCK inhibitor and serum, serum extract, and/or feeders.

14. The method according to claim 10, wherein the ROCK inhibitor is present in a culture medium for up to six days.

15. The method according to claim 10, wherein after differentiation to neural cells or neural precursor cells is induced, the ROCK inhibitor is withdrawn from the culture medium.

16. The method according to claim 10, wherein the serum-free culture medium comprises a material selected from a group consisting of albumin, transferrin, fatty acids, insulin, collagen precursor, trace elements, 2-mercaptoethanol, and 3'-thiolglycerol.

* * * * *